United States Patent
Huttner et al.

(10) Patent No.: US 12,194,105 B2
(45) Date of Patent: Jan. 14, 2025

(54) COMPOSITION AND METHOD FOR NEW ANTIMICROBIAL AGENTS WITH SECONDARY MODE OF ACTION PROVIDED BY CONJUGATION OF AN ANTIMICROBIAL TO A GUANIDINIUM-RICH MOLECULAR TRANSPORTER

(71) Applicant: The Board of Trustees of the Leland Stanford Junior University, Stanford, CA (US)

(72) Inventors: Melanie Huttner, Stanford, CA (US); Paul Wender, Stanford, CA (US); Lynette Cegelski, Palo Alto, CA (US); Xiaoyu Zang, Stanford, CA (US); Alexandra Antonoplis, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 211 days.

(21) Appl. No.: 16/968,834

(22) PCT Filed: Feb. 21, 2019

(86) PCT No.: PCT/US2019/018928
§ 371 (c)(1),
(2) Date: Aug. 10, 2020

(87) PCT Pub. No.: WO2019/165051
PCT Pub. Date: Aug. 29, 2019

(65) Prior Publication Data
US 2024/0016945 A1    Jan. 18, 2024

Related U.S. Application Data

(60) Provisional application No. 62/633,368, filed on Feb. 21, 2018.

(51) Int. Cl.
| | |
|---|---|
| A61K 47/64 | (2017.01) |
| A61K 38/14 | (2006.01) |
| A61K 47/54 | (2017.01) |
| A61P 31/04 | (2006.01) |

(52) U.S. Cl.
CPC ........... *A61K 47/645* (2017.08); *A61K 38/14* (2013.01); *A61K 47/541* (2017.08); *A61P 31/04* (2018.01)

(58) Field of Classification Search
None
See application file for complete search history.

(56) References Cited

U.S. PATENT DOCUMENTS

| | | | |
|---|---|---|---|
| 7,462,687 B2 | 12/2008 | Greenwald et al. | |
| 8,536,147 B2 | 9/2013 | Welle | |
| 2006/0166867 A1* | 7/2006 | Lapidot | A61K 31/7048 514/2.7 |
| 2016/0303184 A1* | 10/2016 | Haldar | A61P 31/04 |
| 2017/0348337 A1* | 12/2017 | Schmidt | A61K 47/64 |

FOREIGN PATENT DOCUMENTS

| | | |
|---|---|---|
| EP | 2576594 B1 | 12/2017 |
| WO | WO2016177899 | 11/2016 |
| WO | WO2017067642 | 4/2017 |

OTHER PUBLICATIONS

Miller ("Antibiotic Resistance and Regulation of the Gram-Negative Bacterial Outer Membrane Barrier by Host Innate Immune Molecules," mBio, 2016, 7(5):e01541-16) (Year: 2016).*
Noorlis et al. ("Antibiotic resistance and biosafety of Vibrio cholerae and Vibrio parahaemolyticus from freshwater fish at retail level," International Food Research Journal 18(4): 1523-1530 (2011)) (Year: 2011).*
Alexandra et al., (2019) "Vancomycin-Arginine Conjugate Inhibits Growth of the Carpaenem-Resistant *E. coli* and Targets Cell-Wall Synthesis" vol. 14, pp. 2065-2070. ACS Chemical Biology.
Alexandra et al., (2018) "A Dual-Function Antibiotic-Transporter Conjugate Exhibits Superior Activity in Sterilizing MRSA Biofilms and Killing Persister Cells", vol. 140, pp. 16140-16151. Journal of the American Chemical Society.
Agnieszka et al., (2017) "Studies of vancomycin-transportan conjugates", VI Ogolnopoiska Konferencja Miodych Naukowcow: czlowiek, nauka, srodowisko, Gdansk, pp. 29-30.
Bahnsen, et al., (2013) "Antimicrobial and cell-penetrating properties of the penetratin analog: Effect of sequence and secondary structure", vol. 1828, pp. 223-232. Biochimica et Biophysica Acta.
Jones, et al., (2012) "Cell entry of cell penetrating peptides: tales of tails wagging dogs",vol. 161, No. 2, pp. 582-591, Journal of controlled release, Elsevier, Amsterdamn, NL.
Junqiu et al., (2015) Antimicrobial activities and action mechanism studies of transportan 10 and its analogue against multidrug-resistant bacteria, vol. 21, pp. 599-607. Journal of Peptide Sience.
Kozlowska et al. (2017) "Participants of the 6th National Conference of Young Scientists" Human Science Environment, Gdańsk, pp. 1-34.

* cited by examiner

*Primary Examiner* — Christina Bradley
(74) *Attorney, Agent, or Firm* — Pamela J. Sherwood; Bozicevic, Field & Francis LLP

(57) ABSTRACT

Antibiotic agents conjugated to a guanidinium-rich molecular transporter (GR-MoTr) are provided. The drug conjugates show surprising increases in efficacy compared to the unconjugated drug in difficult-to-treat bacterial infections including biofilms, stationary and persister cells, and multi-drug resistant bacteria, as well as intracellular bacteria.

7 Claims, 9 Drawing Sheets

COMPOSITION AND METHOD FOR NEW ANTIMICROBIAL AGENTS WITH SECONDARY MODE OF ACTION PROVIDED BY CONJUGATION OF AN ANTIMICROBIAL TO A GUANIDINIUM-RICH MOLECULAR TRANSPORTER

CROSS REFERENCE

This application claims the benefit and is a 371 application of PCT Application No. PCT/US2019/018928, filed Feb. 21, 2019, which claims benefit of U.S. Provisional Application No. 62/633,368, filed Feb. 21, 2018, which are incorporated herein by reference in their entirety.

BACKGROUND

Methicillin-resistant *Staphylococcus aureus* (MRSA) is the leading cause of mortality from antibiotic-resistant infections in the United States and is estimated to be responsible for >50% of all hospital-acquired/associated infections in Asia, and North and South America. MRSA predominantly manifests as skin and soft tissue infections (SSTIs), and when left untreated, MRSA infections may spread hematogenously, resulting in life-threatening diseases. The propensity of MRSA to form biofilms and persister cells has been linked to recurrent infections and chronic diseases. Biofilms consist of slow-growing bacterial cells encased in a self-produced extracellular matrix, while persister cells are dormant, highly antibiotic-tolerant cells that may exist in a planktonic or biofilm state. The emergence of recurrent MRSA infections in both hospital and community settings, coupled to a 90% decline in new antibiotic approvals over the last 30 years by the FDA, renders treatment of MRSA a formidable challenge.

Vancomycin is a glycopeptide antibiotic produced by *Streptococcus orientalis*, and is generally regarded as a first-line therapy for hospitalized patients with MRSA SSTIs. The antibiotic binds to the D-Ala-D-Ala end of lipid II in the peptidoglycan layer of the cell wall, thereby sterically hindering cell wall biosynthesis and inhibiting bacterial growth. In vivo, vancomycin exhibits a slow bactericidal mode of action compared to beta-lactams, resulting in inefficient clearance of infection, and in some cases clinical failure. To achieve an effective concentration at the site of infection, vancomycin is commonly administered intravenously with high and frequent doses, increasing the risk of side effects such as nephrotoxicity, ototoxicity and renal toxicity. The prolonged duration of vancomycin therapy may also select for resistant and/or dormant bacterial survivors, further complicating treatment.

To evade vancomycin's effects, bacteria harboring vancomycin resistance genes replace the D-Ala-D-Ala termini of the cell wall precursor with D-Ala-D-Lac to prevent vancomycin from binding. In addition to being unable to treat resistant pathogens with D-Ala-D-Lac termini, vancomycin can only exert its efficacy on actively growing bacterial cells with a propagating cell wall. Therefore, infections consisting of slow-growing cells, such as infections containing biofilms or persister cells, are unable to be eradicated by vancomycin. This inefficacy may result in chronic infection, where surviving slow-growing bacteria switch to an active growth state and spread to previously uncolonized niches. Vancomycin also poorly penetrates mammalian cells, thereby allowing pathogens such as MRSA to invade and persist intracellularly to avoid vancomycin treatment. Lastly, vancomycin exhibits a relatively slow bactericidal mode of action against infectious agents, resulting in inefficient clearance of infection, and in some cases clinical failure.

Improvement in antibiotic efficacy is of great interest. Antibiotic conjugates with enhanced efficacy are provided herein.

SUMMARY OF THE INVENTION

Antibiotic agents and methods of use are provided, wherein antibiotic agents comprise a guanidinium-rich molecular transporter (GR-MoTr) conjugated to the antibiotic. The drug conjugates show surprising increases in efficacy compared to the unconjugated drug in difficult-to-treat bacterial infections including biofilms, stationary and persister cells, and multi-drug resistant bacteria, as well as intracellular bacteria. In some embodiments the bacteria are Gram-positive bacteria. In some embodiments the bacteria are methicillin-resistant *Staphylococcus aureus* (MRSA).

In some embodiments the antibiotic is a glycosylated cyclic or polycyclic nonribosomal peptide, including without limitation vancomycin, teicoplanin, telavancin, ramoplanin, decaplanin, oritavancin, dalbavancin, etc. In some embodiments the antibiotic is vancomycin or a derivative thereof. In some embodiments the GR-MoTr is conjugated to vancomycin or a derivative thereof at the C-terminus, at the readily derivatizable carboxylic acid functional group that is not involved in vancomycin's mode of action.

In some embodiments the conjugated antibiotic has the structure, where the GR-MoTr may be directly conjugated to vancomycin, or may be conjugated through a linker:

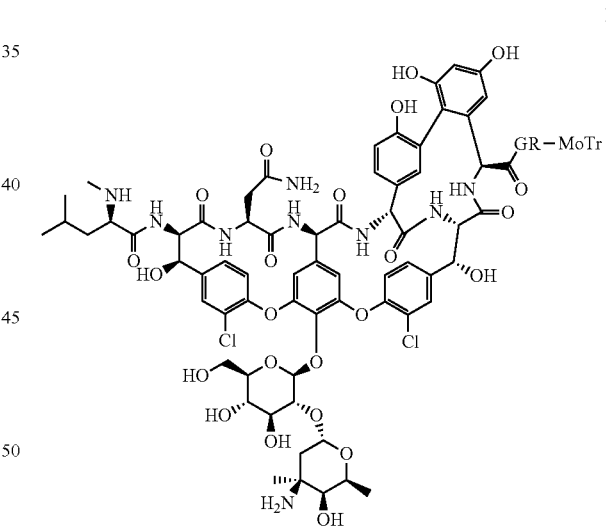

I

In some embodiments the GR-MoTr comprises from about 1 to about 16 guanidinium head groups, for example from around 1 to 8 guanidinium head groups, from about 4 to 8 guanidinium head groups, and may have a carbamate, polycarbonate, glutaramide, polyamine or peptide backbone. In some embodiments the GR-MoTr is an oligomer comprising from about 1 to about 16 arginines, from about 4 to 12 arginines, from about 6 to about 8 arginines, and may comprise 8 arginines. In some embodiments a poly-arginine GR-MoTr consists of from about 7 to about 9 arginines, which may be L-arginine, D-arginine, or a combination thereof. In certain embodiments the GR-MoTr is D-octa-arginine.

In some embodiments the GR-MoTr-conjugated drug is more than 10-fold more active than the unconjugated drug in eradicating MRSA biofilms; in some embodiments more than 25-fold more active. In some embodiments the GR-MoTr-conjugated drug is more than 10-fold more active than the unconjugated drug in eradicating MRSA persister cells; in some embodiments more than 100-fold more active, in some embodiments more than 1000-fold more active, or more. In some embodiments the GR-MoTr-conjugated drug is more than 10-fold more active than the unconjugated drug in eradicating vancomycin-resistant bacteria; in some embodiments more than 100-fold more active. In some embodiments the GR-MoTr-conjugated drug is more than 50% more active than the unconjugated drug in reducing the bacterial load in an intracellular infection. In some embodiments a conjugated drug has enhanced activity against specific Gram-negative bacteria, which include without limitation *Vibrio* sp.

The GR-MoTr-conjugated drug can provide other benefits in delivering an effective dose of antibiotic for treatment of, for example, stationary and persistent bacterial cells, biofilms, intracellular infections, vancomycin-resistant cells, stationary-phase and persistent MRSA cells, MRSA biofilms, etc. at concentrations that are non-toxic to human skin and red blood cells. The GR-MoTr-conjugated drug can be provided in an effective topical dose. The GR-MoTr conjugated antibiotic exhibits a much faster rate-of-killing than the unconjugated drug, where, for example, the period of time required to eradicate an infection is decreased by at least about 2-fold relative to the length of time for treatment with the unconjugated drug. After just 0.5 h in media the conjugated drug eradicated 3-orders of magnitude more bacteria than the unconjugated drug.

In some embodiments, a method of treating a bacterial infection is provided, where the infection may be present in a mammalian host, the method comprising: determining that an infection is caused at least in part by the presence of a biofilm, stationary and/or persistent bacteria, and contacting the bacteria causing the infection with an effective dose of a GR-MoTr-conjugated antibiotic, where the efficacy in eradicating the infection at the effective dose is at least 5-fold higher than the efficacy of the unconjugated antibiotic at the same dose. In some embodiments the infection is treated in the absence of toxicity to the mammalian host cells. In some such embodiments, the antibiotic is vancomycin or a derivative thereof, including the compound of structure I. In some such embodiments the GR-MoTr is oligo-arginine, including without limitation oligo-D-arginine of from about 4 to about 9 arginines in length.

In some embodiments, a method of treating a bacterial infection is provided, where the infection may be present in a mammalian host, the method comprising: determining that an infection is caused at least in part by the presence of a biofilm, stationary and/or persistent bacteria, and contacting the bacteria causing the infection with an effective dose of a GR-MoTr-conjugated antibiotic for a period of time sufficient to treat the infection.

In some embodiments an infection treated by the methods described herein comprises Gram-positive bacteria, including without limitation *staphylococci* sp., *streptococci* sp., *enterococci* sp., *C. diptheriae*, *B. anthracis*, *C. difficile*; and specifically may include *Staphylococcus aureus*, methicillin-resistant *S. aureus* (MRSA), multidrug-resistant *Staphylococcus epidermidis* (MRSE), etc. In some embodiments an infection treated by the methods described herein comprises Gram-negative bacteria, including without limitation *Vibrio cholerae*. The infection may be present in vitro or in vivo and may include, without limitation, skin wound treated topically, as well as internal infections.

In some embodiments a pharmaceutical composition comprising a conjugated antibiotic of the invention as an active agent and a pharmaceutically acceptable excipient is provided. The formulation can be provided, for example, as a unit dose formulation, in a dose that is effective for treating persister or stationary bacteria, biofilms, MRSA, MRSE, etc. The formulation may be administered to a patient suffering from a microbial infection.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

(FIG. 3A) Time-kill experiments for V and V-r8 (both 20 µM) and lysostaphin (1.25 µg/ml, 10×MIC) wherein bacteria were harvested from nutrient broth, treated with compound in PBS, and subsequently enumerated for cell viability by growth on nutrient agar plates. Assay detection limit=2.3. (FIG. 3B) Possible membrane damage was evaluated among cells treated with V, V-r8 (both 20 µM) or lysostaphin (1.25 µg/ml, 10×MIC) using SYTOX Green as a fluorescent probe and indicator of cell damage. Compound data was normalized to cell-only control data.

(FIG. 4A) Confocal microscopy showed bacteria treated with 5 µM FI-V-r8 exhibited approximately twice as much fluorescent signal as 5 µM FI-V treated ones. (FIG. 4B) FACS showed quantitative difference in the signal brightness between FI-V-r8 and FI-V treated bacteria. With Trypan Blue (TB) quenching the extracellular fluorescence, approximately 45% of fluorescence was retained in FI-V-r8 treated bacteria, where FI-V was fully quenched. Each bar represents median normalized fluorescence values from N=2 experiments, where populations of ~2500 cells were analyzed for each treatment in both experiments. Data was normalized to highest fluorescence value in each experiment, and normalized values were compiled for overall median determination. Error bars, if applicable, represent the IQR. (FIG. 4C) FACS showed quantitative difference in the brightness between FI-V-r8 and FI-V protoplasts treated with 1 µM compound prior to protoplast formation. Each bar represents median normalized fluorescence values from N=2 experiments, where populations of ~1500 cells were analyzed for each treatment in both experiments. Data was normalized to highest fluorescence value in each experiment, and normalized values were compiled to determine an overall median. Error bars, if applicable, represent the IQR.

Figures 9, 10:
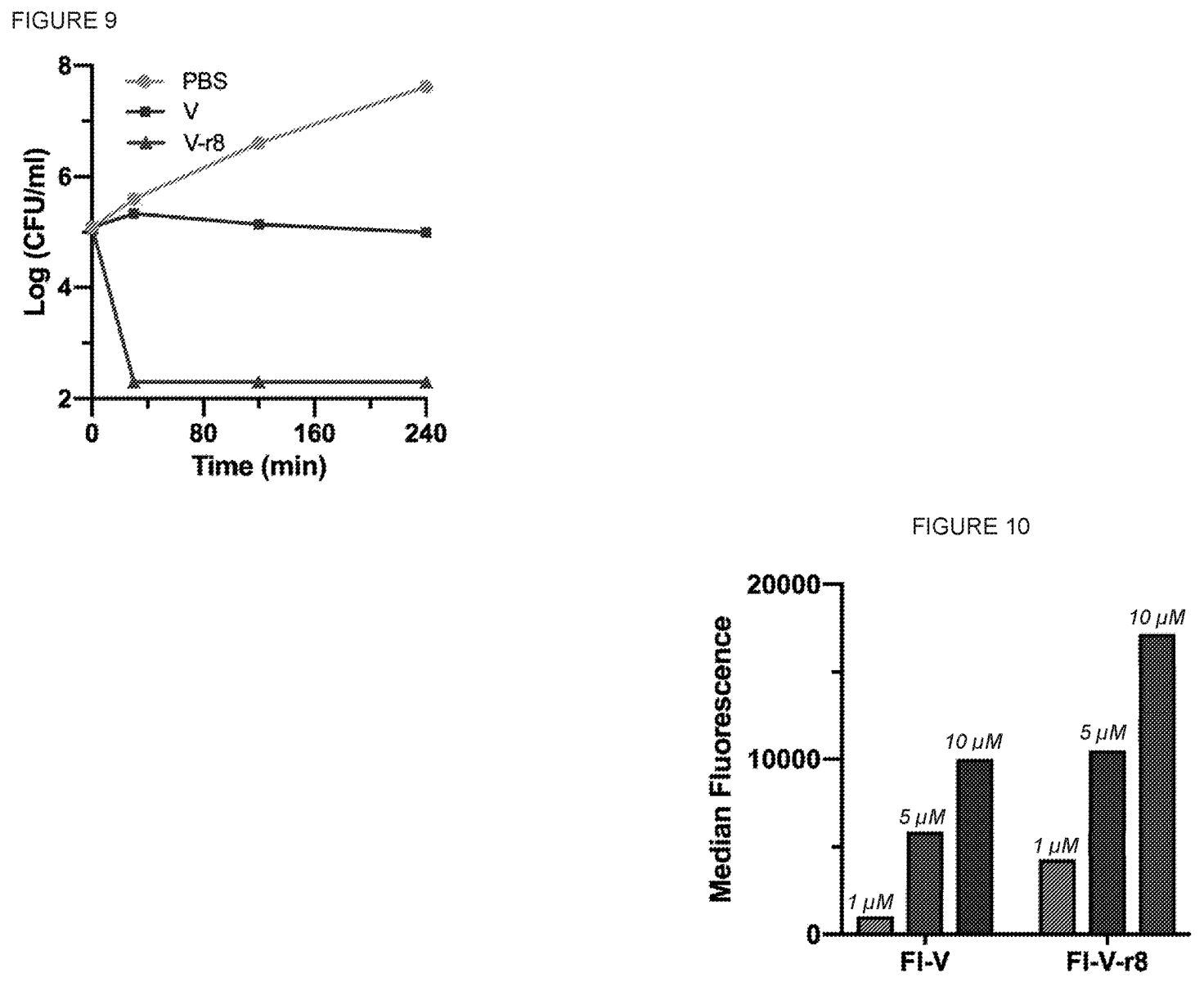

FIG. 9. Influence of V and V-r8 (both at 20 µM) on cell viability for MRSA USA400 MW2 in MHB. V-r8 eradicated MRSA to the CFU/ml detection limit (Assay detection limit=2.3 Log(CFU/ml)). Data points represent median of biological triplicates from a representative experiment; all experiments were repeated on a different day to ensure reproducibility.

FIG. 10. Whole-cell fluorescence analysis of USA400MW2 treated with FI-V-r8 or FI-V. Cells treated with FI-V and FI-V-r8 exhibit concentration-dependent fluorescence after washing away extracellular excess compound as determined by FACS. Each bar represents the median fluorescence obtained from a population of ~2500 cells. Results shown are representative of experiments reproduced on different days.

(FIG. 11A) Treatments were performed at 20 µM in media. (FIG. 11B) Treatments were performed at 2×MIC in PBS. Kan refers to kanamycin, a FDA-approved aminoglycoside. Data points are from a representative experiment. Detection limit=2.3 Log (CFU/ml).

DETAILED DESCRIPTION OF THE EMBODIMENTS

Figure 1:
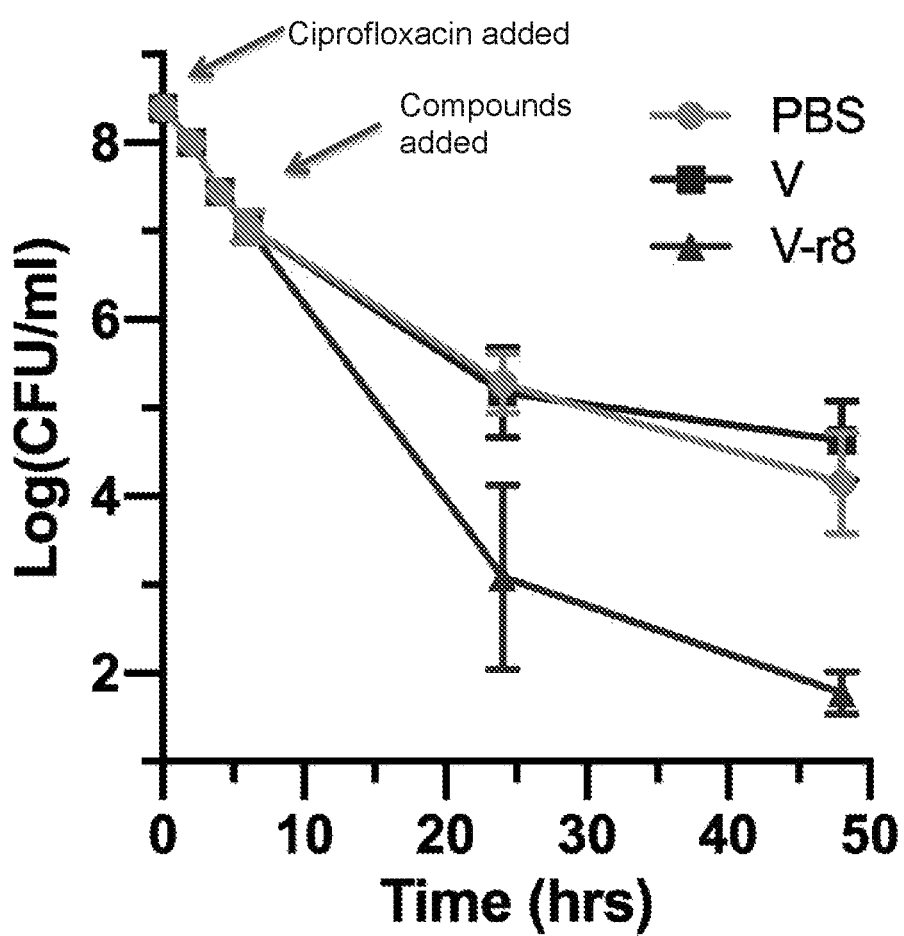
FIG. 1. Time-kill study of MRSA USA300 LAC persister cells treated with vancomycin and V-r8. MRSA persister cells were generated by treatment with ciprofloxacin at 40 µM for 6 h. Vancomycin or V-r8 (TFA salt) was then introduced at a concentration of 10 µM. Data points are median Log(CFU/ml) values from 2 independent experiments (N=2) where treatments were performed in singlicate. Error bars represent IQR. Detection limit: 1 Log(CFU/ml).

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The term "guanidinium rich molecular transporter", or GR-MoTr, as used herein, refers to oligomers or short-length polymers of from 1 to up to 16 subunits, a portion of which have attached guanidinium groups. Examples include, without limitation, those described in U.S. Pat. No. 7,169,814; WO 2017/083637; US Patent publication 20070078078; US Patent publication 20150118704; US Patent publication 20100280219; US Patent publication 20070078094; US Patent publication 20100160239, each herein specifically incorporated by reference. The GR-MoTr is effective to enhance the transport rate of a conjugated antibiotic across a biological membrane relative to the transport rate of the antibiotic alone.

For example, a GR-MoTr may be an oligomer of the following formulae: poly $G^*$, $(G^*S^pG^*)_nG^*$, $(G^*S^p)_nG^*$, $(G^*S^pS^p)_nG^*$ and $(G^*S^pS^pS^p)_nG^*$. "$G^*$" in the formulae is a guanidino-containing subunit and "$S^p$" is a subunit (or spacer) that does not contain a guanidino or amidino moiety. The subscript "n" is an integer ranging from 2 to 25. The letter "$S^p$" can represent a natural or non-natural amino acid, or any other subunit described below that is devoid of a guanidino or amidino group. For those embodiments in which $S^p$ is an amino acid, the amino acid can be essentially any compound having (prior to incorporation into the transport moiety) an amino group ($NH_2$ or NH-alkyl) and a carboxylic acid group ($CO_2H$) and not containing either a guanidyl or amidinyl moiety. Examples of such compounds include D and L-alanine, D and L-cysteine, D and L-aspartic acid, D and L-glutamic acid, D and L-phenylalanine, glycine, D and L-histidine, D and L-isoleucine, D and L-lysine, D and L-leucine, D and L-methionine, D and L-asparagine, D and L-proline, D and L-glutamine, D and L-serine, D and L-threonine, D and L-valine, D and L-tryptophan, D and L-hydroxyproline, D and L-tyrosine, sarcosine, β-alanine, γ-amino butyric acid and ε-amino caproic acid. In each of the above formulae, each $S^p$ will be independent of any other $S^p$ present in the transport moiety, though in some embodiments, all $S^p$ groups can be the same.

In some embodiments the GR-MoTr comprises from about 1 to about 16 guanidinium head groups, for example from around 1 to 8 guanidinium head groups, from about 4 to 8 guanidinium head groups, and may have a carbamate, polycarbonate, glutaramide, polyamine or peptide backbone. In some embodiments the GR-MoTr is an oligomer comprising from about 1 to about 16 arginines, from about 4 to 12 arginines, from about 6 to about 8 arginines, and may comprise 8 arginines. In some embodiments a poly-arginine GR-MoTr consists of from about 7 to about 9 arginines, which may be L-arginine, D-arginine, or a combination thereof. In certain embodiments the GR-MoTr is D-octaarginine.

Antibiotics. Any of a number of antibiotics are suitable for conjugation, or can be modified to be rendered suitable for use in the subject compounds. Classes of antibiotics include, for example, penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; glycopeptides; etc.

Glycopeptide antibiotics are a class of drugs of microbial origin that are composed of glycosylated cyclic or polycyclic nonribosomal peptides. Significant glycopeptide antibiotics include the anti-infective antibiotics vancomycin, teicoplanin, telavancin, ramoplanin and decaplanin. Derivatives of vancomycin include, for example, oritavancin and dalbavancin (both lipoglycopeptides). Telavancin is a semi-synthetic lipoglycopeptide derivative of vancomycin (approved by FDA in 2009). Other vancomycin analogs are disclosed, for example, in WO 2015022335 A1 and Chen et al. (2003) PNAS 100(10): 5658-5663, each herein specifically incorporated by reference.

Gram-positive bacteria. Gram-positive organisms (including bacteria of the genera *Staphylococcus, Streptococcus* and *Enterococcus*) are among the most common bacterial causes of clinical infection. This is primarily due to their association with a diverse spectrum of pathology, ranging from mild skin and soft tissue infections (SSTIs) to life-threatening systemic sepsis and meningitis. Although a number of antimicrobial agents already exist for the treatment of such diseases, emerging issues such as antimicrobial resistance (AMR) and and an increase in hospital-acquired infections have created a need for antimicrobials with novel spectra of activity and pharmacokinetic (PK) profiles.

Included as organisms of particular concern are *Staphylococci* sp., *Streptococci* sp., *Enterococci* sp., *C. diptheriae, B. anthracis, C. difficile*; and specifically may include methicillin-resistant *Staphylococcus aureus* (MRSA), which is resistant to almost all β-lactam antibiotics; glycopeptide-resistant *Enterococci* (GRE), multidrug resistant (MDR) *Streptococcus pneumoniae*; MDR *Streptococcus agalactiae; Streptococcus pyogenes; Enterococcus faecium, Staphylococcus aureus*, multidrug-resistant *Staphylococcus epidermidis* (MRSE), etc.

The term "MRSA" as used herein refers generally to a strain of *Staphylococcus aureus* that is resistant to a large group of antibiotics called the beta-lactams, which include the penicillins and the cephalosporins. Specific examples of beta-lactam antibiotics include methicillin, dicloxacillin, nafcillin, and oxacillin. MRSA is sometimes referred to as multidrug-resistant *Staphylococcus aureus* or oxacillin-resistant *Staphylococcus aureus* (ORSA).

*Staphylococcus aureus* (*S. aureus*) is a cause of a variety of conditions in humans, including skin infections (e.g. folliculitis, styes, cellulitis, impetigo, and furunculosis), pneumonia, mastitis, phlebitis, meningitis, scalded skin syndrome, osteomyelitis, urinary tract infections, and food poisoning. Methicillin resistance is caused by the acquisition of an exogenous gene mecA that encodes penicillin-binding protein (PBP2a or PBP2'), which exhibits a low affinity for β-lactam antibiotics. The mecA gene also is found in coagulase-negative *Staphylococcus* strains that are less pathogenic than *S. aureus*. These strains include *S. epidermidis, S. haemolyticus, S. saprophyticus, S. capitis, S. warneri, S. sciuri* and *S. caprae*. An additional mec gene, named mecC, was discovered which also confers beta-lactam resistance.

Vancomycin-resistant *Enterococcus* is another significant threat to public health. Six different types of vancomycin resistance are shown by *enterococcus*: Van-A, Van-B, Van-C, Van-D, Van-E and Van-G. The mechanism of resistance to vancomycin found in *enterococcus* involves the alteration of the peptidoglycan synthesis pathway. The D-alanyl-D-lactate variation results in the loss of one hydrogen-bonding interaction (four, as opposed to five for D-alanyl-D-alanine) being possible between vancomycin and the peptide. The D-alanyl-D-serine variation causes a six-fold loss of affinity between vancomycin and the peptide, likely due to steric hindrance.

Gram-negative bacteria. Gram-negative bacteria are characterized by their cell envelopes, which are composed of a thin peptidoglycan cell wall sandwiched between an inner cytoplasmic cell membrane and a bacterial outer membrane. The Gram-negative bacteria include *Escherichia coli*, and many pathogenic bacteria, such as *Pseudomonas aeruginosa, Neisseria gonorrhoeae, Chlamydia trachomatis, Yersinia pestis*, and *Vibrio cholerae*. They are an important medical challenge, as their outer membrane protects them from many antibiotics.

Gram-negative bacteria are intrinsically resistant to vancomycin because their outer membranes are impermeable to large glycopeptide molecules, with the exception of some non-gonococcal *Neisseria* species. Surprisingly, vancomycin conjugates described herein are effective against certain Gram-negative bacteria, including without limitation *V. cholerae*.

Biofilm. A biofilm is an accumulation of microorganisms (bacteria, fungi, and/or protozoa, with associated bacteriophages and other viruses) embedded in a polysaccharide matrix and adherent to solid biological or non-biotic surfaces. Biofilms are medically important, accounting for over 80 percent of hospital-acquired microbial infections in the body. Examples include infections of the oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, percutaneous sutures; and tracheal and ventilator tubing. The microorganisms tend to be far more resistant to antimicrobial agents and to be particularly difficult for the host immune system to render an appropriate response.

Biofilms are remarkably difficult to treat with antimicrobials. Antimicrobials may be readily inactivated or fail to penetrate into the biofilm. In addition, bacteria within biofilms have increased (up to 1000-fold higher) resistance to antimicrobial compounds, even though these same bacteria are sensitive to these agents if grown under planktonic conditions.

Biofilms play a significant role in the transmission and persistence of human disease and have emerged as virulence hallmarks of serious and persistent infectious diseases, including cystic fibrosis pneumonia, infective endocarditis, urinary tract infection (UTI), periodontitis, chronic infections of the middle ear, and infections of medical devices such as intravenous catheters and artificial joints. Currently available antibiotics often fail to eradicate biofilm-associated bacteria, necessitating multiple and intense antibiotic treatment regimens that drive the evolution of resistant pathogens and the exhaustion of last-resort antibiotics. As a consequence, biofilm-associated infections are the cause of significant morbidity and mortality in the clinic.

A biofilm is an assemblage of microbial cells that is closely associated with a surface and enclosed in a matrix of material, including polysaccharides, DNA, and proteins. Noncellular materials such as mineral crystals, corrosion particles, clay or silt particles, or blood components, depending on the environment in which the biofilm has developed, may also be found in the biofilm matrix. Biofilm-associated organisms also differ from their planktonic (freely suspended) counterparts with respect to the genes that are transcribed. Biofilms may form on a wide variety of surfaces, including living tissues, indwelling medical devices, industrial or potable water system piping, or natural aquatic systems.

The solid-liquid interface between a surface and an aqueous medium provides an ideal environment for the attachment and growth of microorganisms. The solid surface may have several characteristics that are important in the attachment process. The extent of microbial colonization appears to increase as the surface roughness increases. This is because shear forces are diminished, and surface area is higher on rougher surfaces. The physicochemical properties of the surface may also exert a strong influence on the rate and extent of attachment. Microorganisms attach more rapidly to hydrophobic, nonpolar surfaces such as Teflon and other plastics than to hydrophilic materials such as glass or metals.

Other characteristics of the aqueous medium, such as pH, nutrient levels, ionic strength, and temperature, may play a role in the rate of microbial attachment to a substratum. Several studies have shown a seasonal effect on bacterial attachment and biofilm formation in different aqueous systems. This effect may be due to water temperature or to other unmeasured, seasonally affected parameters.

Cell surface hydrophobicity, presence of fimbriae and flagella, and production of EPS all influence the rate and extent of attachment of microbial cells. The hydrophobicity of the cell surface is important in adhesion because hydrophobic interactions tend to increase with an increasing nonpolar nature of one or both surfaces involved (i.e., the microbial cell surface and the substratum surface). Most bacteria are negatively charged but still contain hydrophobic surface components. Fimbriae, i.e., nonflagellar appendages other than those involved in transfer of viral or bacterial nucleic acids, contribute to cell surface hydrophobicity. Most fimbriae that have been examined contain a high proportion of hydrophobic amino acid residues. Fimbriae play a role in cell surface hydrophobicity and attachment, probably by overcoming the initial electrostatic repulsion barrier that exists between the cell and substratum. A number of aquatic bacteria possess fimbriae, which have also been shown to be involved in bacterial attachment to animal cells.

Other cell surface properties may also facilitate attachment. Several studies have shown that treatment of adsorbed cells with proteolytic enzymes caused a marked release of attached bacteria, providing evidence for the role of proteins in attachment. The O antigen component of lipopolysaccharide (LPS) has also been shown to confer hydrophilic properties to Gram-negative bacteria.

Persisters are dormant variants of regular cells that form stochastically in microbial populations and are highly tolerant to antibiotics. Persisters may be the main culprit responsible for the recalcitrance of chronic infectious disease to antimicrobial therapy. Persister cells usually comprise about 1% of the populations in the stationary-phase growth state and in biofilms.

These persister cells comprise a subpopulation of bacteria that become highly tolerant to antibiotics and reach this state without undergoing genetic change. Also, the number of persister cells depends on the growth stage. Persister cells in biofilms appear to be responsible for the recalcitrance of chronic infections, since antibiotics kill the majority of cells; however, persisters remain viable and repopulate biofilms when the level of antibiotics drops.

A model for the formation of persister cells is that toxin-antitoxin (TA) pairs are primarily responsible, as they induce a state of dormancy that enables cells to escape the effects of antibiotics. TA systems typically consist of a stable toxin (always a protein) that disrupts an essential cellular process (e.g., translation via mRNA degradation) and a labile antitoxin (either RNA or a protein) that prevents toxicity. For example high persistence (hip) mutants have been identified. The hipBA locus constitutes a toxin-antitoxin locus, and the HipA toxin inactivates the translation factor EF-Tu by phosphorylating it.

Minimum inhibitory concentrations (MICs) are defined as the lowest concentration of an antimicrobial that will inhibit the visible growth of a microorganism after overnight incubation, and minimum bactericidal concentrations (MBCs) as the lowest concentration of antimicrobial that will prevent the growth of an organism after subculture on to antibiotic-free media. For example, see Andrews (2001) J Antimicrob Chemother. 48 Suppl 1:5-16'

Minimal biofilm eradication concentration (MBEC) is defined as the lowest concentration of an antimicrobial agent required to eradicate a biofilm.

Methods of Use and Formulations

Methods are provided for the use of GR-MoTr-conjugated antibiotics as antimicrobial agents, including without limitation conjugates of vancomycin and vancomycin derivatives and analogs. In some embodiments the conjugate is as shown in structure I. Such conjugates can be administered alone or in combination with other active agents to a patient suffering from or predisposed to infections that are resistant or tolerant to conventional antibiotics, including infections resistant to vancomycin, methicillin, etc. The infection is treated by contacting the infectious bacterial cell population with a dose and for a period of time sufficient to reduce the population of microbial pathogens, in vivo or in vitro, including for example medical surfaces.

An effective dose may be the dose that achieves substantial depletion or eradication of the bacterial cell population, which result in the killing of substantially all of the bacterial cells, e.g. at least about 99%, at least about 99.9%, at least about 99.99%, or more. The effective dose may be based on the MIC, or MBEC, although is typically a higher dose to ensure eradication. The effective dose of a conjugated antibiotic is generally at least about 5-fold less than the effective dose for the corresponding non-conjugated antibiotic, and may be 10-fold less, 50-fold less, 100-fold less, or less. The effective time for eradication is also decreased, for example decreased at least 2-fold, at least about 3-fold, at least about 4-fold, at least about 5-fold, or more.

An effective dose of a conjugated antibiotic may be a dose that achieves a concentration at the target site of at least about 0.01 µM, at least about 0.1 µM, at least about 1 µM, at least about 5 µM, at least about 10 µM, at least about 50 µM, at least about 100 µM, at least about 500 µM, at least about 1 mM, at least about 5 mM, at least about 10 mM.

In some embodiments, the effective daily dose can range from about 0.5 mg to about 500 g, for example at least about 0.5 mg, at least about 1 mg, at least about 5 mg, at least about 10 mg, at least about 50 mg, at least about 100 mg, at least about 500 mg, at least about 1 g, at least about 5 g, at least about 10 g, at least about 50 g, at least about 100 g, and not more than about 500 g.

In some embodiments an infection for treatment comprises a bacterial cell population in which at least about 5% of the bacteria are resistant or tolerant to antibiotics, at least about 10%, at least about 20%, at least about 30%, at least about 50%, at least about 75%, at least about 85%, at least about 95% resistant or tolerant bacteria, where resistant or tolerant bacteria may include, for example: persister cells; MRSA; MRSE; GRE; ORSA; Gram-negative bacteria when the antibiotic is vancomycin or a derivative thereof; biofilms; vancomycin resistant bacteria; etc.

In some embodiments the infection is present on the skin, i.e. a wound. In such embodiments, a topical formulation is optionally utilized for treatment. An advantage of the conjugated antibiotic provided herein is the enhanced bioavailability for topical formulations that is provided.

In some embodiments the antibiotic resistant or tolerant bacteria are present as a biofilm. In some embodiments the biofilm is substantially comprised of Gram-positive bacteria. In some embodiments a biofilm is present on implantable medical devices, which are particularly susceptible to biofilm formation.

In some embodiments, the effective daily dose is provided in a unit dosage formulation in any increment. As non-limiting illustrative examples: administration of one 1.6 mg capsule, two 800 µg capsules, etc. can be performed twice in one day to deliver a daily dose of 3.2 mg; or thrice in one day to deliver a daily dose of 4.8 mg. As another non-limiting example, the use of 1 mg capsules facilitates any dose (e.g., a daily dose) with a multiple of (1 mg) (e.g., 2 mg, 3 mg, 4 mg, etc.)

A treatment regime can entail administration daily (e.g., once, twice, thrice, etc. daily), every other day (e.g., once, twice, thrice, etc. every other day), semi-weekly, weekly, once every two weeks, once a month, etc. In another example, treatment can be given as a continuous infusion. Unit doses are usually administered on multiple occasions. Intervals can also be irregular as indicated by monitoring clinical symptoms. Alternatively, the unit dose can be administered as a sustained release formulation, in which case less frequent administration is required. Dosage and frequency may vary depending on the patient. It will be understood by one of skill in the art that such guidelines will be adjusted for localized administration, e.g. intranasal, inhalation, rectal, etc., or for systemic administration, e.g. oral, rectal (e.g., via enema), i.m. (intramuscular), i.p. (intraperitoneal), i.v. (intravenous), s.c. (subcutaneous), transurethrally, and the like.

The conjugated antibiotic can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of GR-MoTr-antibiotic conjugate includes use in combination with another therapeutic agent, e.g., a bacteriocidal or bacteriostatic agent. Therapeutic formulations can be prepared for storage by mixing the GR-MoTr-antibiotic conjugate with optional physiologically acceptable carriers, excipients or stabilizers (Remington's Pharmaceutical Sciences 16th edition, Osol, A. Ed. (1980)), in the form of lyophilized formulations or aqueous solutions. The GR-MoTr-antibiotic conjugate composition will be formulated, dosed, and administered in a fashion consistent with good medical practice. The "effective amount" to be administered will be governed by considerations such as those cited above (e.g., severity of disease etc.), and is the minimum amount necessary to prevent and/or reduce the targeted biofilm.

Formulations of GR-MoTr-antibiotic conjugates are administered to a host suffering from or predisposed to a microbial infection. Administration may be topical, localized or systemic, depending on the specific microorganism, preferably it will be localized. Generally the dose of biofilm inhibitor will be sufficient to decrease the microbial population in the biofilm by at least about 50%, usually by at least 1 log, and may be by 2 or more logs of release. The compounds of the present invention are administered at a dosage that reduces the microbial population while minimizing any side-effects. It is contemplated that the composition will be obtained and used under the guidance of a physician for in vivo use.

GR-MoTr-antibiotic conjugates are also useful for in vitro formulations to dissolve microbial biofilms. For example, biofilm inhibitors may be added to hospital equipment, e.g. ventilation, water processing, etc.

The susceptibility of a particular microbe to GR-MoTr-antibiotic conjugates may be determined by in vitro testing, as detailed in the experimental section. Typically a culture of the microbe is combined with agents at varying concentrations for a period of time sufficient to allow the GR-MoTr-antibiotic conjugates to act, usually between about one hour and one day. The attached microbes are then counted, and the level of viability determined.

Various methods for administration may be employed. The formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific biofilm inhibitor to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously.

Formulations

The GR-MoTr-antibiotic conjugate can be incorporated into a variety of formulations for therapeutic administration. In some embodiments the formulation comprises a GR-MoTr-antibiotic conjugate of Formula I, where the GR-MoTr may be directly conjugated to vancomycin, or may be conjugated through a linker

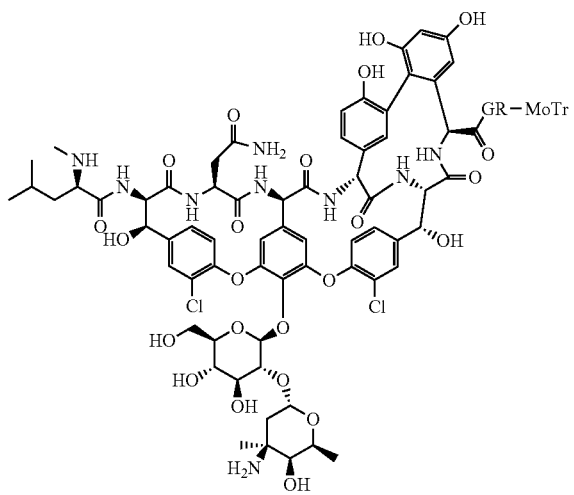

In some embodiments the GR-MoTr comprises from about 1 to about 16 guanidinium head groups, for example from around 1 to 8 guanidinium head groups, from about 4 to 8 guanidinium head groups, and may have a carbamate, polycarbonate, glutaramide, polyamine or peptide backbone. In some embodiments the GR-MoTr is an oligomer comprising from about 1 to about 16 arginines, from about 4 to 12 arginines, from about 6 to about 8 arginines, and may comprise 8 arginines. In some embodiments a poly-arginine GR-MoTr consists of from about 7 to about 9 arginines, which may be L-arginine, D-arginine, or a combination thereof. In certain embodiments the GR-MoTr is D-octa-arginine.

Suitable linkers are known in the art (see, for example, Wong, S. S., Ed., Chemistry of Protein Conjugation and Cross-Linking, CRC Press, Inc., Boca Raton, Fla. (1991). In particular, carbamate, ester, thioether, disulfide, and hydrazone linkages are generally easy to form and suitable for most applications. Other linkers such as trimethyl lock (see Wang et. al. J. Org. Chem., 62:1363(1997) and Chandran et al., J. Am. Chem. Soc., 127:1652 (2005)), quinine methide linker (see Greenwald et. al. J. Med. Chem., 42:3657 (1999) and Greenwald et. al. Bioconjugate Chem., 14:395 (2003)), diketopiperazine linker and derivatives of thereof are also of interest of this invention. Ester and disulfide linkages may be preferred if the linkage is to be readily degraded in a biological environment, after transport of the substance across the cell membrane. Ester linkers can also be cleaved extracellularly with the help of extracellular esterases. Various functional groups (hydroxyl, amino, halogen, thiol etc.) can be used to attach the antibiotic to the GR-MoTR or to a linker. Groups which are not known to be part of an active site of the antibiotic are preferred.

More particularly, the compounds can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, transurethral, etc., administration. The biofilm inhibitors may be systemic after administration or may be localized by the use of an implant or other formulation that acts to retain the active dose at the site of implantation.

The compounds of the present invention can be administered alone, in combination with each other, or they can be used in combination with other known compounds (e.g., antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing biofilm inhibitors is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 μg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Attachment of a Guanidinium-Rich Molecular Transporter to Vancomycin Enables Rapid Cell Association and Killing of MRSA Biofilms and Persister Cells New antibiotic strategies are urgently needed to target slow-growing and non-replicating pathogenic bacteria. Here we report the synthesis and characterization of a vancomycin-octaarginine conjugate (V-r8), designed to improve delivery of vancomycin to difficult-to-treat bacterial populations. We have discovered that V-r8 eradicates MRSA biofilms and persister cells, and exhibits a unique, previously undescribed mode of action compared to vancomycin. In vivo, V-r8 significantly reduced MRSA biofilm loads in a murine skin wound model within a five-hour treatment. Based on its rapid and potent activity against infectious bacteria, we propose V-r8 as a promising agent for the treatment of persistent MRSA infections.

To improve vancomycin delivery and activity, we designed, synthesized and evaluated a new vancomycin derivative. Recently, chemical modifications to vancomycin, including addition of membrane-active groups along with modifications to the D-Ala-D-Ala binding pocket, have notably improved vancomycin's antibacterial activity. Our approach is applicable to such vancomycin analogs, but our derivative consists of vancomycin itself conjugated to a cell-penetrating guanidinium-rich molecular transporter (GR-MoTr), specifically an octa-(D)-arginine (r8) motif.

Although the use of a highly polar, polycationic agent to cross non-polar membranes at first appeared counter-intuitive, our extensive studies have guided the formulation of chemical and biophysical descriptions of how this transport process occurs, in essence driven by the number and spatial array of guanidinium groups and their initial association with negatively charged cell surface carboxylic acids, sulfates and phosphates.

Our group and others have utilized a range of GR-MoTrs, including arginine-rich peptides and guanidinium-rich non-peptidic agents to deliver a variety of cargos, including antimicrobials, chemotherapeutics, peptides, and oligonucleotides into cells in vitro and in vivo. Covalent attachment of an oligoarginine to a chemotherapeutic has been shown to overcome multidrug resistance in mammalian cells and animals by changing the mechanism of uptake of the chemotherapeutic, thereby avoiding Pgp export while also rendering it more water-soluble as a transporter conjugate. GR-MoTr conjugates successfully cross a variety of mammalian barriers, including in vivo delivery into skin. GR-MoTrs have been conjugated to antimicrobial agents, producing conjugates with varying efficacy depending on the antimicrobial agent, transporter, and pathogen. Additionally, GR-MoTrs have delivered fluorescent cargos into non-mammalian cells, including parasites, algae cell walls, and bacteria.

We hypothesized that conjugation of a GR-MoTr to an antibiotic would produce a conjugate with improved activity arising from enhanced access to and association with bacterial cell-envelope constituents and from penetration of biofilm barriers. Such conjugates may also be used to deliver antibiotics to intracellular targets for those antibiotics that have intracellular targets. Given the urgent need for new antibacterial strategies and the promise of opening up a field of new antibacterial design strategies based on GR-MoTr enhanced or enabled antibiotic conjugates, we designed and evaluated the therapeutic potential of a vancomycin-Gr-MoTr conjugate for clinical applications.

Results and Discussion

Figure 5:
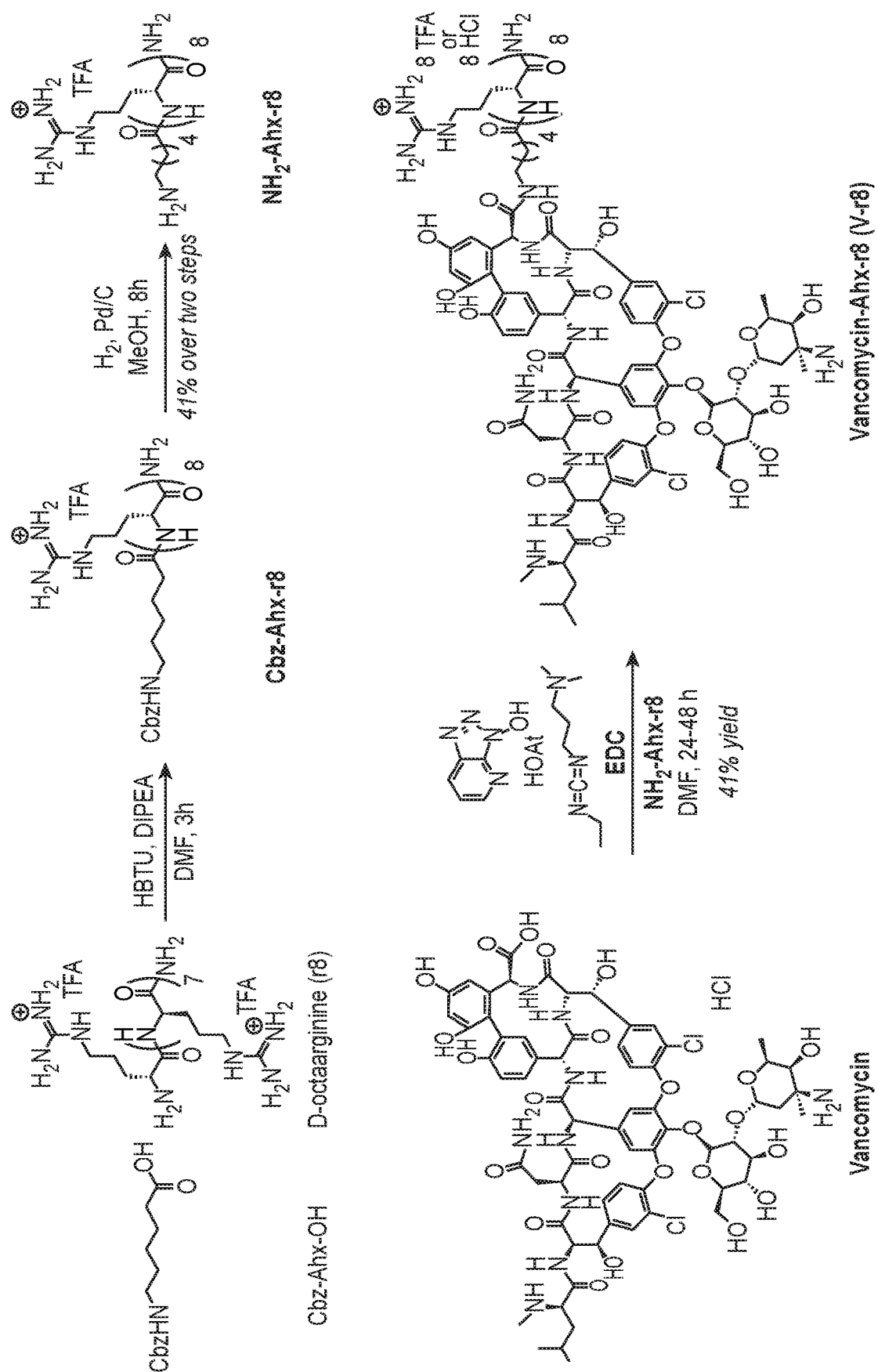
FIG. 5. Synthesis of a novel vancomycin conjugate, V-r8.
Figure 6:
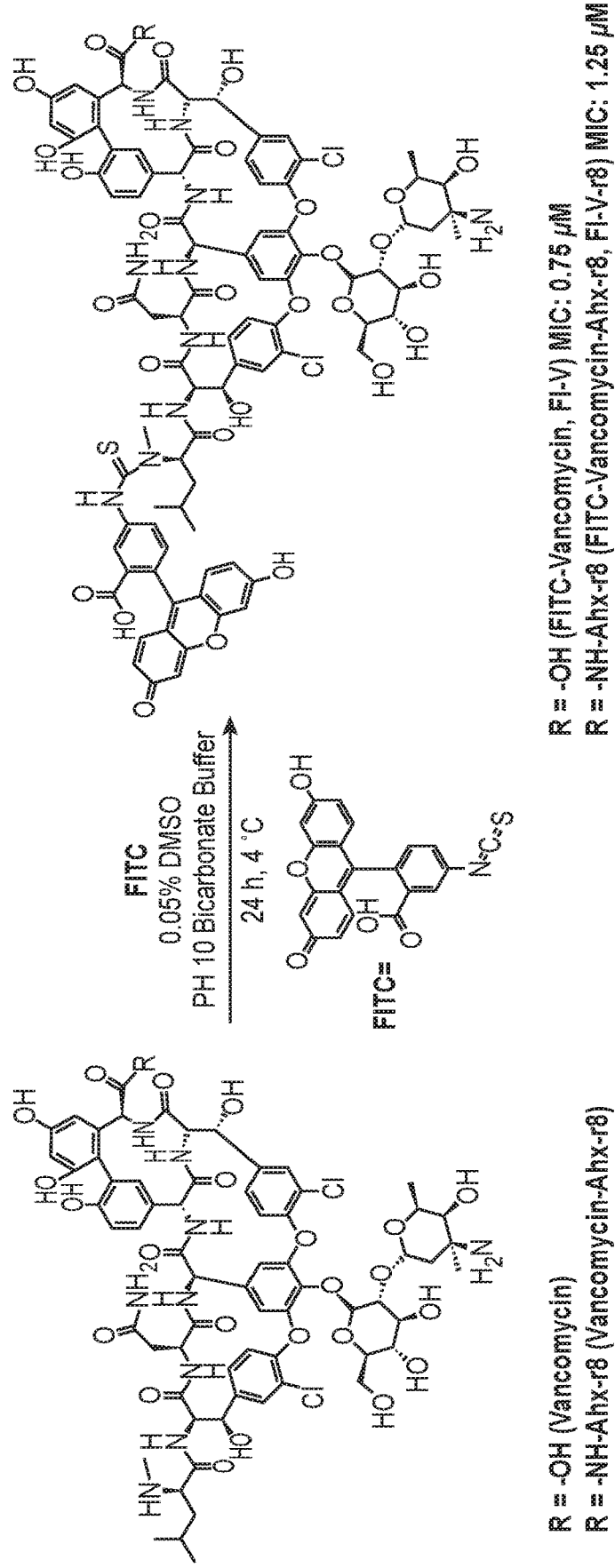
FIG. 6. Design and synthesis of fluorescently labeled vancomycin (FI-V) and vancomycin-D-octaarginine (FI-V-r8).
Figure 7:
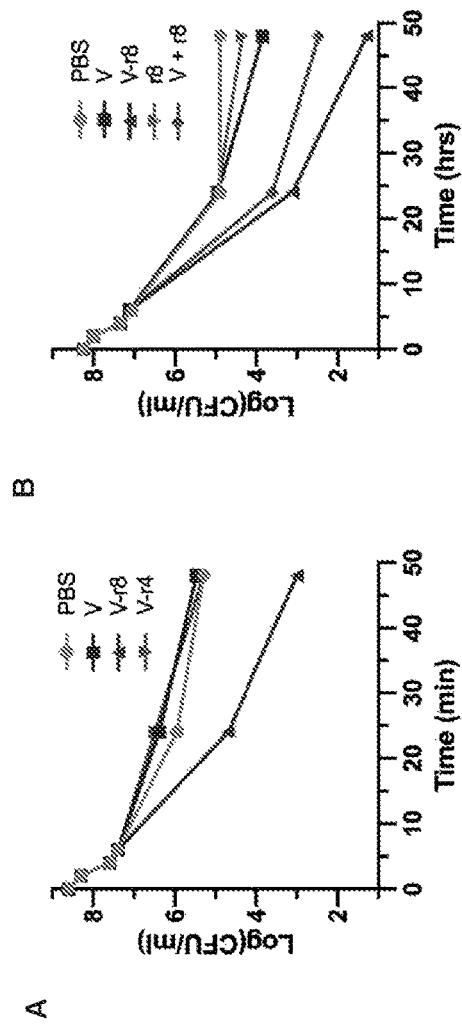
FIG. 7A-7B. Evaluation of V-4 and V+r8 activity against MRSA USA300 LAC persister cells in comparison with V-r8. MRSA persisters were generated by treatment with ciprofloxacin at 40 µM for 6 h. V, V-r4 and V-r8 treatments were performed in singlicate at 10 µM. Assay detection limit=1 log.
Figure 8:
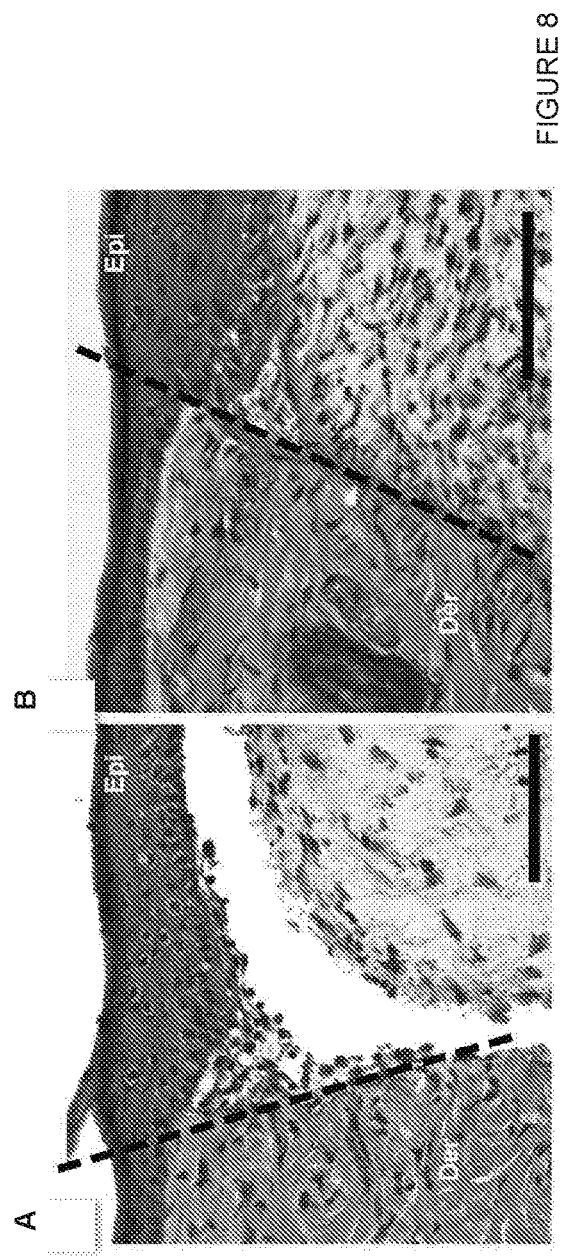
FIG. 8A-8B. To examine in vivo cytotoxicity, sterile wounds were generated and inoculated only with water (FIG. 8A) or 0.05% V-r8 (FIG. 8B) in the absence of bacteria. Wound tissue was harvested after 3 days and examined by Hematoxylin & Eosin staining. The epidermis and dermis layers from mice treated with 0.05% V-r8 appeared similar to those from water treated mice and did not exhibit signs of necrosis. Wound healing was also comparable between groups as indicated by dermal granulation tissue formation and epidermal healing. A small increase in neutrophil infiltration was observed in V-r8 treated mice as compared to untreated mice. Epi: skin epidermis; Der: skin dermis. Scale bar represents 100 µm. Images are representative of 3 independent samples.
Figure 11:
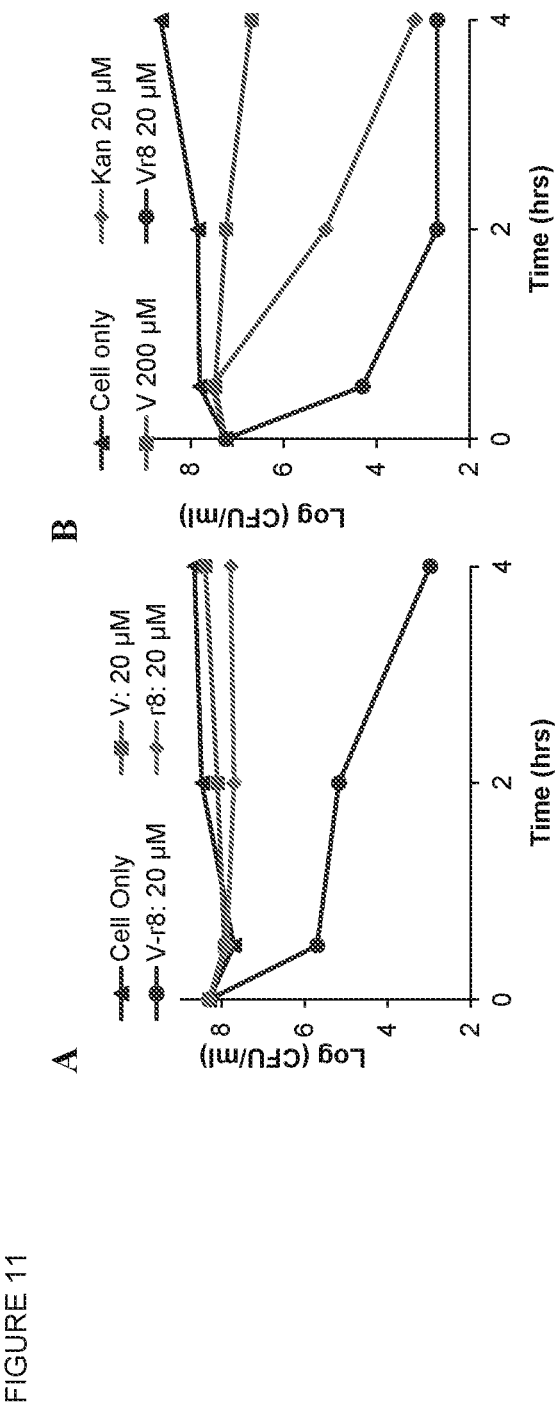
FIG. 11A-11B. Time-kill study of *V. cholerae* treated with compounds.

Design and Synthesis of V-r8. For the synthesis of the vancomycin-GR-MoTr conjugate, we attached a cell-penetrating peptide with a linker to the C-terminus of vancomycin at the readily derivatizable carboxylic acid functional group that is not involved in vancomycin's mode of action. D-octaarginine (r8) was first coupled to N-protected aminohexanoic (Ahx) acid, followed by deprotection with $H_2$ and Pd/C to yield $NH_2$-Ahx-r8 (FIG. 5). Unnatural D-amino acids were chosen for their increased stability to proteolysis. An 8-residue peptide was selected based upon considerations of optimal uptake efficiency and step economical synthesis. The transporter, $NH_2$-Ahx-r8, was conjugated to the C-terminus of vancomycin to produce V-r8 (Scheme 1) using an optimized procedure from previously reported coupling conditions (see Mishra et al. (2015) Org. Biomol. Chem. 13, 7477-7486). V-r8 was purified as a TFA salt by reverse-phase HPLC and characterized by HRMS and $^1$H-NMR. V-r8 was also generated as an HCl salt, as HCl salts of vancomycin derivatives have been reported to exhibit improved MICs and superior mammalian cell compatibility compared with TFA salts. A vancomycin conjugate with only four D-arginines (V-r4) was additionally synthesized to evaluate the impact of peptide length on the conjugate's efficacy.

Antibacterial Activity Against Planktonic Bacteria and Biofilms. Vancomycin is effective at inhibiting growth of planktonic *S. aureus*, including MRSA, but is generally not effective in eradicating *S. aureus* biofilm bacteria. We evaluated V-r8 in comparison with vancomycin in planktonic and biofilm-associated antibacterial assays. V-r8 as either the TFA or HCl salt displays single digit micromolar antimicrobial activity against three *S. aureus* strains, including two MRSA strains (Table 1). This activity against planktonic bacteria is comparable to that of vancomycin. We hypothesized that the addition of a GR-MoTr would improve the delivery and efficacy of vancomycin against *S. aureus* biofilms. Thus, the activities of V-r8 and vancomycin were compared in antibacterial biofilm assays using the Calgary biofilms device (Ceri et al. (1999) J. Clin. Microbiol. 37, 1771-1776). V-r8 demonstrated >31-fold better potency in media and 160-fold better potency in PBS over vancomycin (V) in diminishing growth of biofilm-associated bacteria, yielding minimum biofilm eradication concentrations (MBECs) of 2.5-16 µM (Table 1). As controls, r8 on its own was unable to eradicate biofilms in the concentration range tested, and a non-covalent 1:1 mixture of V+r8, while exhibiting some activity against biofilms as compared to vancomycin, was much less potent than V-r8. Additionally, the shorter peptide derivative, V-r4, was not as effective as V-r8 in assays with either planktonic or biofilm bacteria, indicating that the number of arginine residues selected for derivatization is important. Overall, these results demonstrate that the covalent conjugation of r8 to vancomycin enhances its ability to eradicate biofilm-associated bacteria.

has been previously documented, and further emphasizing the efficacy of V-r8 in eradicating difficult-to-treat, chronic MRSA infections. Additionally, although not as potent as V-r8, a noncovalent V+r8 mixture showed enhanced killing of persister cells. However, no activity against persister cells was observed for r8 alone or for V-r4.

Figure 2:
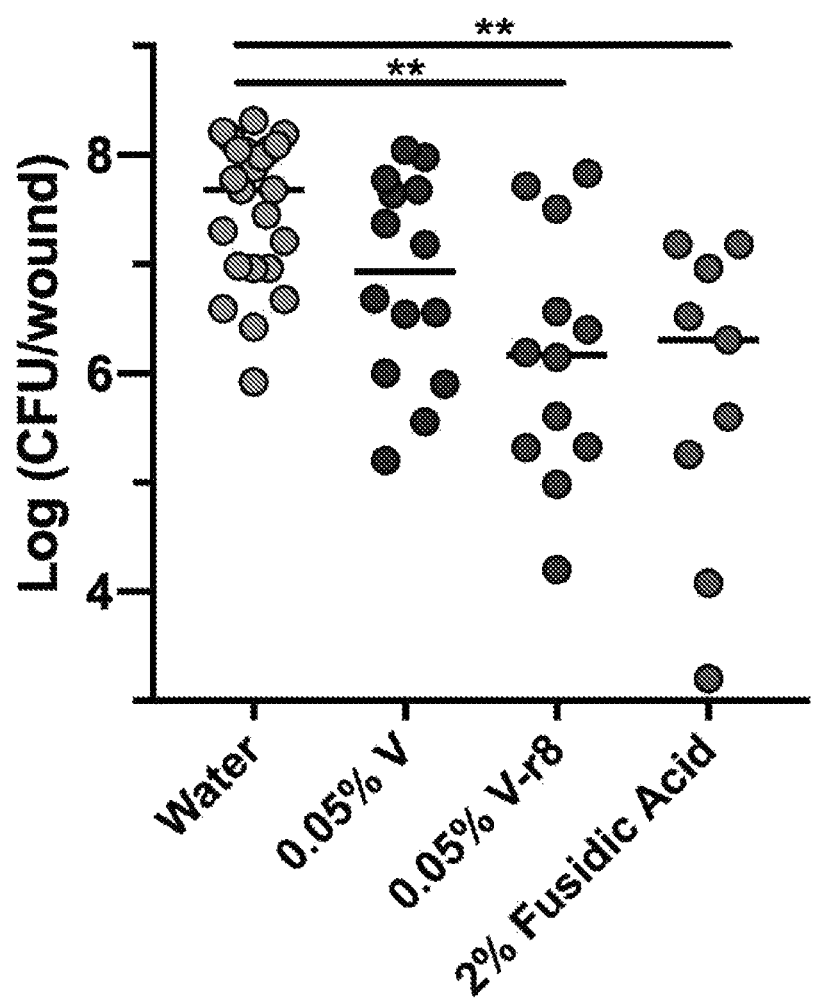
FIG. 2. In vivo evaluation of compounds in a skin wound biofilm model. 10 µL of water or compound dissolved in PBS was administered to the biofilm wound on the back of an 8-week old male C57BL/6 mouse 24 hpi with USA300 LAC. Mice were sacrificed 5 h post-treatment and the bacteria in the wound were enumerated. Each data point represents Log(CFU/wound) from one mouse. Bars represent the median bacterial load. Data were compiled from 2-3 independent experiments containing 4-5 animals per treatment group. Statistical analysis was performed using the non-parametric Kruskal-Wallis test with Dunn's post ad-hoc test for intergroup comparisons. ** P<0.01.

Antibacterial Activity Against Biofilms In Vivo. MRSA is a major causative agent of wound and soft tissue infections. Thus, in vivo studies were designed to evaluate the ability of V-r8 to treat biofilm infections in a mouse wound excisional model. To determine optimal V-r8 treatment times for in vivo experiments, we additionally examined the influence of treatment time on biofilm eradication in vitro using the Calgary biofilm assay. V-r8 was able to eradicate 98% of the biofilm-associated MRSA USA 300 LAC after a 5-hr treatment at 16 and 32 µM, whereas vancomycin was ineffective. These observations predicted a similar treatment time would be effective in vivo. Given that V-r8 exhibited rapid killing of biofilms in vitro, an in vivo study was next explored. Mice were infected with USA300 LAC for 24 hours using an established biofilm wound procedure, followed by a 5 hour topical treatment. We observed a significant reduction in biofilm bacterial load at 0.05% V-r8 compared to untreated mice (FIG. 2). Vancomycin was administered at a matched percent solution for comparison to V-r8. A reduction in median CFU/wound counts was observed for vancomycin treatment as compared to untreated mice, but this difference was not statistically significant. V-r8 was also compared to fusidic acid, commonly used for MRSA skin infections in Asia, Europe, and Australia, that has limited efficacy because of emerging resistance. Therefore, new antimicrobial compounds with comparable activity in vitro and in vivo could be used to address this therapeutic need. Significantly, 0.05% V-r8 was as effective as 2% fusidic acid in reducing the bacterial load in wounds after a 5 h treatment,

TABLE 1

Median (Interquartile Range, IQR) MIC and MBEC values from a minimum of 2 independent experiments. ¹MBEC treatment was performed in PBS for V-r8 HCl in USA300 to mimic in vivo compound administration.

| Strain | Minimum Inhibitory Concentration (MIC), µM | | | | Minimum Biofilm Eradication Concentration (MBEC), µM | | | |
|---|---|---|---|---|---|---|---|---|
| | Vancomycin | V-r8 8TFA | V-r8 8HCl | r8 | Vancomycin | V-r8 8TFA | V-r8 8HCl | r8 |
| MSSA (29213) | 0.5 (0) | 1.6 (0.5) | 1.25 (0.3) | 60 (20) | ≥500 | 16 (10) | 16 (10) | >80 |
| MRSA (USA400MW2) | 0.5 (0) | 0.94 (0.2) | 0.75 (0.1) | 20 (0) | ≥500 | 10 (5) | 10 (6) | >80 |
| MRSA (USA300LAC) | 0.5 (0) | 2.0 (0.1) | 1.5 (0.5) | 40 (0) | ≥400 | 9.5 (10) | 2.5 (2)* | >80 |

Antibacterial Activity Against Persister Cells. Encouraged by the ability of V-r8 to eradicate biofilm bacteria, we evaluated its ability to kill MRSA USA300 persister cells (Waters et al. (2016) PLOS Pathog. 12, e1006012). Persister cells can be generated in the laboratory by treatment of an exponentially growing bacterial population with a high concentration (10×MIC) of an antibiotic, where the majority of cells are killed, but a remaining fraction survive in a non-replicating dormant state (<1%), yielding a bimodal time-kill curve (Brauner et al. (2016) Nat. Rev. Microbiol. 14, 320-330). After generating persister cells and treating them with V-r8, we observed enhanced killing of persister cells as compared to treatment with vancomycin itself. Remarkably, V-r8 was >1500-fold more efficacious at 20 µM than vancomycin (FIG. 1). Vancomycin was ineffective in eradicating MRSA persister populations, in line with what even with V-r8 employed at a 40-fold lower percent solution. Additionally, in an in vivo open wound toxicity study of 0.05% V-r8 (in the absence of bacteria), no acute toxicity was observed. Histological examination 3-days post treatment indicated absence of necrosis and apoptosis. These results demonstrate that V-r8 can effectively reduce biofilm bacterial loads in a murine wound excisional model.

Time-dependent Killing Assays. To further examine the superior efficacy of V-r8 over vancomycin and gain preliminary insight into its mode-of-action, we evaluated cell viability of MRSA USA400 MW2 bacteria that were harvested from nutrient broth and transferred into PBS with compound added as a function of treatment time. Following treatment, bacteria were spotted on nutrient agar plates without compound to permit enumeration of CFU/mL. This assay identifies compounds that exert cell killing without requiring cell growth. Vancomycin, for example, only inhibits peptidoglycan synthesis if they are actively growing in the presence of the antibiotic (Reynolds (1989) Eur. J. Clin. Microbiol. Infect. Dis. Off. Publ. Eur. Soc. Clin. Microbiol. 8, 943-950 (1989).

Figure 3:
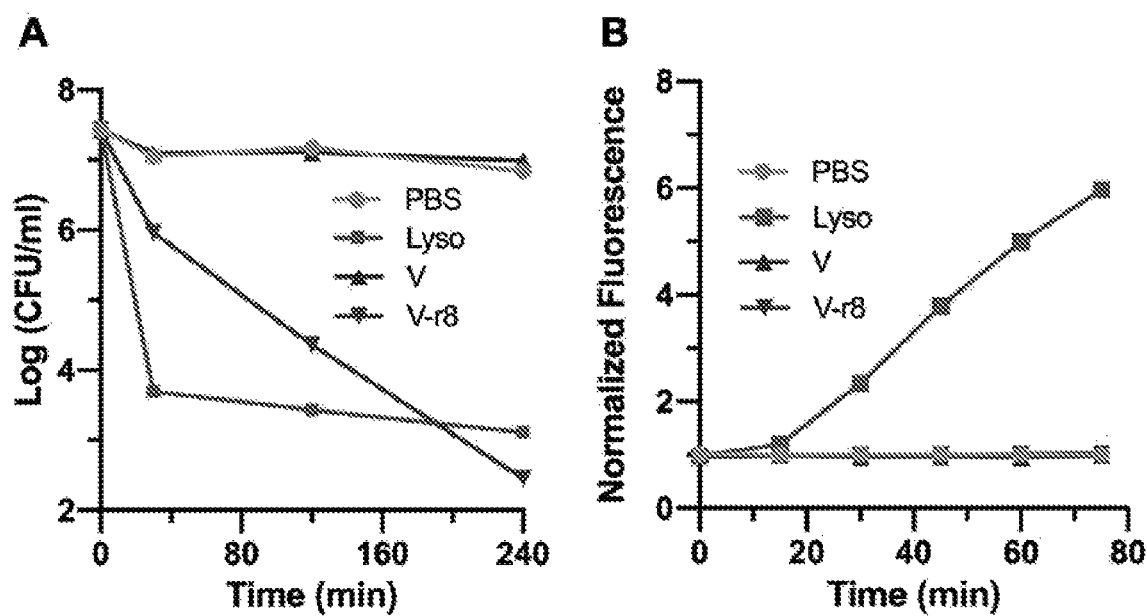
FIG. 3A-3B. V-r8 mode-of-action analysis using stationary-phase MW2. All data points represent the median of biological duplicates from a representative experiment; all experiments were repeated on a different day to ensure reproducibility. V-r8 was the TFA salt, and PBS was used for the cell only control.

As illustrated in FIG. 3A, vancomycin does not instantly kill cells when added to cells in PBS and bacteria are able to grow when transferred to fresh nutrient agar. In striking contrast, V-r8 treatment resulted in bacterial killing down to the assay's detection limit as reflected in reduced cell growth upon transfer to nutrient agar (FIG. 3A). Lysostaphin, an antibacterial enzyme that induces membrane permeabilization, served as a positive control for rapid killing at a concentration equivalent to 10×MIC. We also performed time-kill studies with actively growing MRSA USA400MW2, where an overnight liquid culture was resuspended in Mueller-Hinton Broth and subsequently treated with compounds. We also observed rapid killing by V-r8 in this assay, whereas a reduction in cell viability effected by vancomycin required longer treatment time. The difference in killing time between vancomycin and V-r8 provides insight into the enhanced mode of action for the vancomycin-conjugate.

Evaluation of Membrane Damage. Rapid killing of bacteria in the viability assay above is a common feature of antimicrobial agents such as cationic antimicrobial peptides that physically damage the bacterial membrane, leading to loss of barrier integrity and cell death. Thus, we sought to investigate the impact of V-r8 on MRSA cell membrane integrity using SYTOX Green, a fluorophore that can enter cells when damaged and bind DNA. Lysostaphin was again used as a positive control at 10×MIC. Rapid uptake of SYTOX Green was observed upon treatment with lysostaphin as expected from its effect on membrane permeation. In striking contrast, V-r8 or vancomycin at 20 µM, the maximum concentration tested, exhibited no SYTOX Green uptake (FIG. 3B). The absence of SYTOX Green fluorescence signal after treating with V-r8 shows that unlike other reported vancomycin-conjugates, V-r8 does not induce bacterial membrane damage.

Cellular Localization Studies with Fluorescent Vancomycin and Fluorescent V-r8. Given the unique and contrasting activity of V-r8 compared to vancomycin, as well as the mammalian cell-penetrating ability of a GR-MoTr, we hypothesized a novel mode of action for V-r8, specifically that it crosses the bacterial membrane; binding to D-Ala-D-Ala targets intracellularly. This novel notion supports the observations in FIG. 1 and FIG. 3A involving treatment of slow-growing and non-replicating cells, where V-r8 is effective at killing persister cells and cells that were incubated with V-r8 in PBS and then transferred to fresh nutrient agar without compound for CFU/ml enumeration. If V-r8 were strongly cell-associated and/or internalized, it would be effective when cells reinitiated growth, even with external antibiotic presence is not maintained. To evaluate the localization and association of V-r8 in MRSA, we synthesized fluorescent derivatives of vancomycin (FI-V) and V-r8 (FI-V-r8) using FITC. The fluorescent derivatives retained the antibacterial activity of the corresponding parent compounds (Scheme 2, see Xu et al. (2013) Chin. J. Appl. Chem. 31, 220-224).

Figure 4:
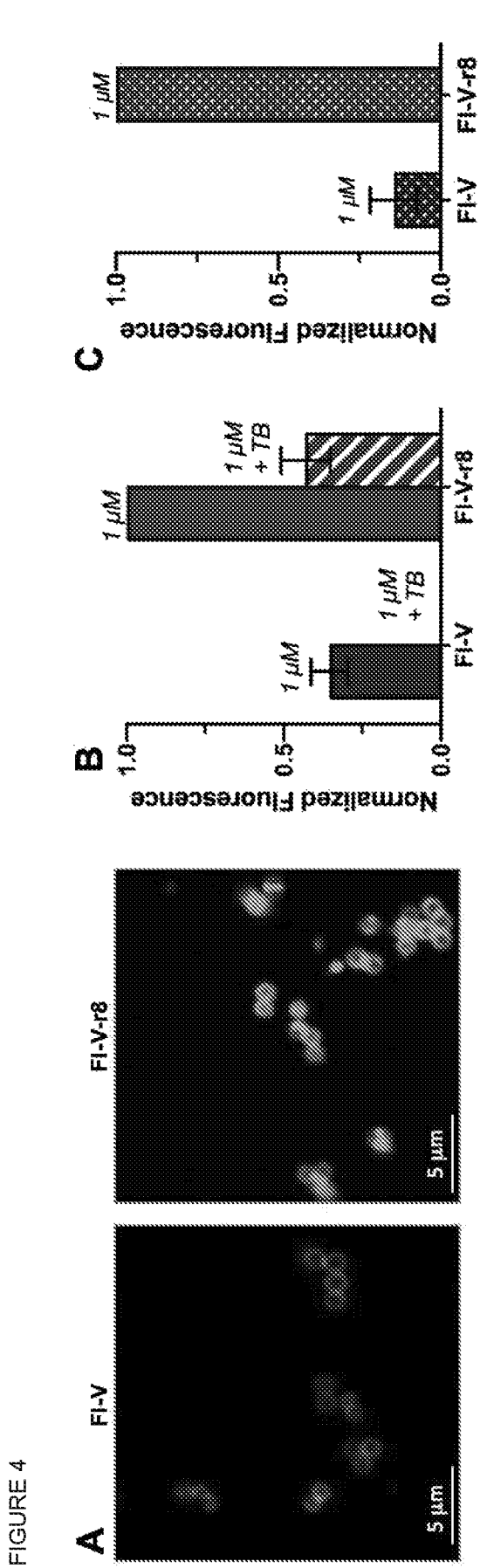
FIG. 4A-4C. USA400 MW2 bacteria treated with FI-V-r8 or FI-V exhibit fluorescent signals with different intensities after washing or quenching.

Previous studies have shown that fluorescently labeled vancomycin localizes to the cell wall and preferentially to cell septa during cell division (Daniel & Errington (2003) Cell 113, 767-776). We treated MW2 bacteria with FI-V or FI-V-r8 at 5 µM and evaluated the uptake and localization of the two compounds. Bacteria treated with FI-V-r8 and washed with PBS exhibited about twice as much fluorescence as compared to FI-V treated bacteria (FIG. 4A). The difference between FI-V and FI-V-r8 observed by confocal microscopy was supported by quantitative analysis using fluorescence activated cell sorting (FACS, FIG. 4B). We also observed concentration-dependent cellular uptake of FI-V and FI-V-r8 by FACS. The increased fluorescent signal for FI-V-r8 treated bacteria reveals that V-r8 exhibits stronger cellular association than vancomycin. However, it does not specifically identify whether V-r8 could have been transported into the cell or externally cell-membrane associated.

To further test our hypothesis that V-r8 could be transported into the cell and target Lipid II intracellularly, we used Trypan Blue as a quenching agent to eliminate fluorescence from fluorophores located extracellularly but associated on the cells' surface. After treatment with Trypan Blue, approximately 50% of the fluorescent signal from FI-V-r8 treated cells remained, which was nearly ten times higher than that of FI-V treated bacteria, as determined by FACS (FIG. 4B), indicating that ~50% of FI-V-r8 was unquenchable. Furthermore, we sought additional biochemical evidence to evaluate the localization of FI-V versus FI-V-r8, and generated MRSA protoplasts by digesting and removing the cell wall through lysostaphin treatment. We observed fluorescence in FI-V-r8 treated cells, but minimal fluorescence in FI-V treated cells, by microscopy and flow cytometry of protoplasts. Specifically, cells treated with 5 µM FI-V-r8 exhibited a greater than 8-fold increase in median fluorescence compared to cells treated with FI-V, which exhibited only baseline level fluorescence (FIG. 4C).

To summarize, FI-V-r8 exhibits strong fluorescence, about half of which is not quenched by an extracellular quenching agent, and maintains fluorescence after digestion of the cell wall, together consistent with internalization of the compound. We find a novel antimicrobial mode of action, wherein V-r8 accumulates at the surface of bacteria and is internalized due to its conjugation to r8. V-r8 is effective in killing biofilm-associated and slowly-growing dormant cells when they attempt to divide by having been locally concentrated on and within cells, which could enable the glycopeptide to interact with D-Ala-D-Ala units at the membrane exoface or intracellular D-Ala-D-Ala targets that were previously inaccessible by vancomycin alone.

The novel vancomycin conjugate, V-r8, readily prepared from vancomycin and r8, exhibits an unprecedented mode of action and clinically desired activities against difficult-to-treat MRSA infections including in vivo biofilms. V-r8 outperformed vancomycin, often by orders of magnitude, in all persister cell and biofilm assays, and demonstrated a faster bactericidal mode of action, tighter membrane association, and intracellular accumulation. V-r8 reduced biofilm loads in vivo, while exhibiting no acute toxicity or damage to skin cells. The ability of V-r8 to treat slow-growing bacterial cells without membrane damage makes it a unique candidate for therapeutic use. Thus, V-r8 is a new antibacterial compound, with activity extendable to other r8 conjugates, that addresses the grand challenge of targeting multi-drug resistant and biofilm-associated pathogens associated with recurrent and chronic Gram-positive bacterial infections.

Supporting Information

TABLE 2

Median (Interquartile Range, IQR) MIC, MBEC values for V-r4 and V + r8 and Log CFU/ml counts per peg on the Calgary Biofilms Device. MIC and MBEC values are medians from a minimum of 2 independent experiments performed in singlicate except for *, which indicates median is from one experiment with two replicates. V-r8 data reproduced from Table 1 in the main text. To represent the enumeration of viable cells harvested per peg, the log CFU/ml values represent the median (IQR) of 23-24 peg biofilms sampled in one experiment.

|  | Minimum Inhibitory Concentration (MIC), μM | | | Minimum Biofilm Eradication Concentration (MBEC), μM | | | log CFU/ml counts per peg |
| --- | --- | --- | --- | --- | --- | --- | --- |
| Strain | V-r8 | V-r4 | V + r8 | V-r8 | V-r4 | V + r8 | |
| MSSA (29213) | 1.6 (0.5) | ND | 0.5 (0) | 16 (10) | ND | 80 (30) | 6.5 (0.3) |
| MRSA (USA400MW2) | 0.94 (0.2) | 2 (0) | 0.5 (0) | 10 (5) | 48 (20)* | >63 | 6.3 (0.2) |
| MRSA (USA300LAC) | 2.0 (0.1) | 3 (1)* | 0.5 (0) | 9.5 (10) | ND | 16 (20) | 6.3 (0.4) |

TABLE 3

Evaluation of biofilm reduction by V and V-r8 in vitro. MRSA USA300 biofilms were grown for 48 h on Calgary Biofilms Device using the MBEC procedure described in methods section. Biofilms were treated for 5 h (instead of 24 h for MBEC determination) with V or V-r8 at 16 or 32 μM in PBS. CFU/ml from remaining viable bacterial cells were plated and enumerated. V-r8 was able to eradicate >99% of MRSA biofilms after 5 h treatments at both 16 and 32 μM. Vancomycin at the same concentrations was ineffective at killing biofilms. Untreated biofilm growth control yielded a Log (CFU/ml) count of 4.5. Assay detection limit = 2 Log. Results are median log CFU/ml counts (IQR) from 2 independent experiments.

|  | Log CFU/ml counts | |
| --- | --- | --- |
| Treatment concentration (μM) | V | V-r8 |
| 0 (PBS only) | 4.5 (0.5) | 4.5 (0.5) |
| 16 | 4.3 (0.3) | 2.2 (0.2) |
| 32 | 5.1 (1.0) | 2.0 (0) |

Additional Information About VRE

Strains with the resistance gene express resistance when they sense the presence of vancomycin and produce D-Ala-D-Lactose instead of D-Ala-D-Ala. This alteration at vancomycin's binding site reduces vancomycin's binding affinity. Vancomycin's MIC increased >1350-fold in VRE *faecium* and >85-fold in VRE *faecalis* (Table X). Impressively, V-r8 (and even V-r4 to a lesser extent) retained low micromolar antimicrobial activity against VRE *faecium*, demonstrating a 128-fold improvement. This improvement is likely attributed to one or both of the following: i) VRE does not sense V-r8 to be like vancomycin and therefore does not alter the production of D-Ala-D-Ala, and/or ii) V-r8 exhibits its potency through an additional mechanism that does not involve binding to D-Ala-D-Ala. Future directions will be aimed at probing V-r8's mode of action.

TABLE 4

Median MIC and MBEC values in μM obtained from a minimum of 2 independent experiments. V + r8 is a 1:1 noncovalent mixture.

|  | E. faecium MICs | | E. faecalis MICs | |
| --- | --- | --- | --- | --- |
| Compound | Van-Susceptible | Van-Resistant | Van-Susceptible | Van-Resistant |
| V | 0.375 | 512 | 1.5 | 128 |
| r8 | >64 | >128 | >64 | >64 |
| V + r8 | 0.5 | 32 | 1.25 | 48 |
| V – r8 TFA | 0.56 | 4 | 2[a] | 32 |
| V – r4 | ND | 8 | ND | ND |

ND = not determined;
[a]Value taken from one trial.

General Methods

Unless otherwise noted, all reactions were run under a nitrogen atmosphere in flame-dried glassware. Reactions were sealed with rubber septa or Teflon™-coated caps and stirred using Teflon™-coated magnetic stir bars. Solid reagents were measured on a Mettler Toledo AB104-S balance. Room temperature indicates an external temperature of 22-25° C.

Anhydrous dimethylformamide (DMF), dimethyl sulfoxide (DMSO) and methanol (MeOH) were obtained from Thermo Fisher. Amine base (DIPEA) were distilled over CaH$_2$ under nitrogen. Reagents were purchase from SERVA (Vancomycin hydrochloride), Bachem (Cbz-Ahx-OH), Thermo Fisher Scientific (fluorescein isothiocyanate), Novabiochem (peptide coupling reagents), Applied Biosystems (peptide resin) and UCB bioproducts (octa-D-arginine). RP-HPLC was carried out using an MeCN:H2O gradient using a Shimadzu Prominence system equipped with a Restek 18 column (5 μm, 21×250 nm) or an Agilent Eclipse XDB-C18 5 μm semi-preparative column (9.4×250 mm). NMR spectra were measured on a Varian INOVA 500 ($^1$H at 500 MHz, $^{13}$C at 125 MHz), a Varian 400 ($^1$H at 400 MHz, $^{13}$C at 100 MHz), or a Varian INOVA 600 MHz ($^1$H at 600 MHz, $^{13}$C at 150 MHz) magnetic resonance spectrometer, as noted. Deuterated solvents were obtained from Cambridge Isotope Laboratories, Inc. $^1$H chemical shifts are reported relative to the residual solvent peak (d4-methanol=3.31 ppm or DMSO=2.50 ppm) as follows: chemical shift (δ), multiplicity (s=singlet, bs=broad singlet, d=doublet, t =triplet, q=quartet, m=multiplet), coupling constant(s) in Hz, integration. $^{13}$C chemical shifts are reported relative to the residual deuterated solvent $^{13}$C signals (d4-methanol=49.00 ppm or DMSO=39.52 ppm). High resolution mass spectra (HRMS) were obtained at the Vincent Coates Mass Spectrometry Laboratory, Stanford, CA 94305. Matrix-assisted laser desorption/ionization (MALDI) were obtained at the Protein and Nucleic Acid Facility (PAN), Stanford, CA 94305.

Experimental Procedures and Characterization Data

Synthesis and Characterization. Cbz-ahx-r8. Cbz-Ahx-OH (17.3 mg, 0.065 mmol, 1 equiv) and TBTU (41.7 mg, 0.13 mmol, 2 equiv) were dissolved in dry DMF (300 μL). To a separate vial was added octa-D-arginine•8TFA (142.7 mg, 0.065 mmol, 1 equiv.) in dry DMF (0.5 mL). Both vials were flushed with nitrogen. The D-octaarginine solution was transferred via a syringe to the flask containing Cbz-Ahx-OH, and rinsed with two 400 μL portions of dry DMF. The reaction mixture was tinted orange. Upon addition of freshly distilled DIPEA (45 μL, 0.26 mmol, 4 equiv.), the reaction mixture turned oranger and clear. The reaction mixture stirred at room temperature under N$_2$ and was monitored by LC-MS and stopped after three hours. The DMF was lyophilized and the reaction mixture was purified by RP-HPLC on a Prep column, 5-70% CH$_3$CN/H$_2$O with 0.1% TFA over 30 min. The appropriate fractions were lyophilized and the product was isolated as a white solid (51.6% yield).

$^1$H-NMR (CD$_3$OD, 600 MHz): δ 8.43-8.09 (m, 8H), 7.34-7.28 (m, 5H), 5.06 (s, 2H), 4.33-4.25 (m, 8H), 3.21 (dd, J=1.2, 0.3 Hz, 16H), 3.10 (t, J=6.6 Hz, 2H), 2.30 (t, J=6.5 Hz, 2H), 2.03-1.62 (m, 34H), 1.51 (t, J=7.2 Hz, 2H), 1.38-1.32 (m, 2H) ppm. $^{13}$C-NMR (CD$_3$OD, 126 MHz): δ 177.08, 176.93, 176.85, 176.74, 176.5, 174.75, 174.59, 174.54, 174.48, 174.1, 163.5, 163.21, 163.19, 162.94, 162.90, 162.88, 162.66, 162.65, 162.63, 162.62, 158.6, 138.4, 129.4, 128.9, 128.6, 119.28, 119.28, 119.27, 119.25, 116.94, 116.93, 116.91, 67.3, 55.65, 55.59, 54.9, 54.3, 41.95, 41.90, 41.6, 36.5, 30.6, 29.76, 29.75, 29.73, 29.62, 29.59, 29.58, 29.56, 29.48, 28.9, 27.4, 26.47, 26.39, 26.33 ppm.

HRMS (ES+m/z): Calculated for $C_{62}H_{119}N_{34}O_{11}^{2+}$: 757.4782 (M+2H)/2. Found: 757.4867 (M+2H)/2.

$T_R$: 14 minutes.

NH$_2$-ahx-r8 Cbx-Ahx-r8•8TFA (45.2 mg, 0.186 mmol, 1 equiv) and Pd/C (2 mg, 10 w/w %) were dissolved in dry methanol (200 μL). The reaction vial was flushed with N$_2$, then H$_2$. The reaction mixture stirred at room temperature under an H$_2$-filled balloon at 1 atm for 5 h, then was filtered through Celite and concentrated in vacuo to yield the deprotected peptide. The peptide was further purified by RP-HPLC on a Prep column, 5-70% CH$_3$CN/H$_2$O with 0.1% TFA over 30 min. The appropriate fractions were lyophilized and the product was isolated as a white solid (64% yield).

$^1$H-NMR (CD$_3$OD, 600 MHz): δ 8.42-8.10 (m, 8H), 4.32-4.29 (m, 8H), 3.21 (m, 16H), 2.92 (t, J=7.1 Hz, 2H), 2.32 (t, J=7.2 Hz, 2H), 2.04-1.66 (m, 36H), 1.43-1.40 (m, 2H) ppm.

$^{13}$C-NMR (CD$_3$OD, 101 MHz): δ 176.6, 176.4, 175.2, 174.73, 174.63, 174.60, 174.52, 174.39, 174.0, 163.1, 162.75, 162.72, 162.71, 55.7, 55.42, 55.28, 55.13, 55.11, 54.93, 54.81, 54.2, 41.96, 41.92, 40.5, 36.3, 30.3, 29.69, 29.64, 29.51, 28.2, 27.1, 26.32, 26.31, 26.16 ppm.

HRMS (ES+m/z): Calculated for $C_{54}H_{114}N_{34}O_{9}^{2+}$: 690.835 (M+2H)/2. Found: 690.4670 (M+2H)/2.

$T_R$: 5.4 minutes.

V-r8 TFA Salt. Vancomycin-HCl (37.1 mg, 0.025 mmol, 1.5 equiv) was added to an oven dried vial and stir bar. HOAt (12.1 mg, 0.089 mmol, 5.4 equiv) and EDC-HCl (16.2 mg, 0.085 mmol, 5.1 equiv) were added to the vial. To a separate vial was added peptide NH$_2$-ahx-r8 (37.7 mg, 0.017 mmol, 1 equiv). Both vials were filled with argon and 0.5 mL dry DMF was added to each vial. The peptide was quantitatively transferred (rinsed twice with 0.2 mL DMF after the first transfer) to the Vancomycin vial for a final concentration of 12 mM of peptide. N-methylmorpholine (10% total volume) was added dropwise and the reaction mixture turned from cloudy white to cloudy yellow. The reaction stirred at room temperature for 24-36 h, at which point the reaction mixture had turned clear. ~1 mL HPLC grade H$_2$O was added slowly to dilute the reaction. The crude mixture was lyophilized overnight. The crude foam was redissolved in 1-1.5 mL dH$_2$O and purified by RP-HPLC on a Semi-Prep column with 5-55% CH$_3$CN/H$_2$O with 0.1% TFA over 30 min. The appropriate fractions were lyophilized and the product was isolated as a TFA salt (41% yield). The compound was stored as frozen aliquots in MQ water at −20° C. Defrosted aliquots would be used within 24 h for experiments. Concentration of aliquots were determined using Nanodrop UV-Vis spectrometer based on Beer's Law (λ=280 nm for vancomycin, c=4200, path length=1 mm). $^1$H-NMR (CD$_3$OD, 500 MHz): δ 9.16-8.74 (m, 1H), 8.25 (dt, J=48.4, 4.9 Hz, 1H), 7.79-7.45 (m, 3H), 7.39-7.09 (m, 2H), 7.09-6.91 (m, 1H), 6.85 (d, J=7.6 Hz, 1H), 6.54-6.28 (m, 1H), 5.81 (d, J=15.6 Hz, 1H), 5.58-5.23 (m, 4H), 4.75-4.63 (m, 1H), 4.63-4.56 (m, 0.25 H), 4.50-4.18 (m, 8H), 4.18-4.01 (m, 1H), 4.00-3.70 (m, 2H), 3.70-3.58 (m, 1H), 3.21 (d, J=11.0 Hz, 12H), 3.02-2.64 (m, 4H), 2.31 (s, 2H), 2.13-2.02 (m, 1H), 2.02-1.55 (m, 30H), 1.54-1.44 (m, 1H), 1.43-1.33 (m, 1H), 1.27-1.16 (m, 2H), 1.10-0.86 (m, 6H) ppm.

$^{13}$C-NMR: (DMSO, 126 MHz) 174.05, 173.05, 172.58, 172.08, 171.87, 170.71, 169.87, 159.82, 159.57, 159.31, 159.06, 157.77, 157.57, 157.01, 155.77, 150.61, 143.15, 138.36, 135.49, 132.60, 127.88, 126.91, 125.05, 122.61, 121.26, 118.89, 116.52, 114.14, 107.05, 105.37, 102.81, 101.91, 97.46, 95.80, 78.86, 77.72, 77.47, 71.41, 70.85, 63.81, 61.93, 60.22, 59.66, 55.66, 54.61, 52.83, 41.14, 35.87, 33.90, 31.88, 29.73, 26.92, 25.68, 25.76, 24.39, 23.48, 22.97, 17.51 ppm.

$^{19}$F-NMR: (CD$_3$OD, 376 MHz): δ-76.9 ppm.

HRMS (ES+m/z): Calculated for $C_{120}H_{185}Cl_2N_{43}O_{32}^{2+}$: 1405.68 (M+2H)/2, $C_{120}H_{186}Cl_2N_{43}O_{32}^{3+}$: 937.45 (M+3H)/3. Found: 1406.1726 (M+2H)/2, 938.0782 (M+3H)/3.

$T_R$: 19.5 minutes

NH$_2$-ahx-r4$^3$. Fmoc-Rink amide resin (169 mg, 0.11 mmol, 1 equiv) was mixed in DMF under nitrogen in a fritted peptide vessel for 20 min. The vessel was drained via vacuum and the Fmoc-protecting group was removed by mixing resin in 8 ml of a 20% piperidine/DMF solution for 30 min. The vessel was drained via vacuum and washed with DMF (2×) and DCM (2×). A Kaiser resin test was performed by adding one drop each of (i) 5 g of ninhydrin in 100 mL ethanol, (ii) 80 g of liquefied phenol in 20 mL of ethanol, (iii) 0.001 M aqueous potassium cyanide in pyridine to a resin sample and the mixture was shaken to mix and heated with a heat gun for 30 seconds. A positive test (indicating a free amine) resulted in blue-colored beads while a negative test (indicating a protected amine) resulted in dark red-colored beads.

After deprotection was complete, Fmoc-D-Arg (pbf)-OH (3.5 equiv) or Fmoc-Ahx-OH (3.5 equiv), HOBT (3.5 equiv), and HBTU (3.5 equiv) were dissolved in 10 mL DMF followed by the addition of DIPEA (10 equiv). The mixture was added to the resin and agitated for 2 h with a stream of nitrogen. The vessel was drained via vacuum and washed with DMF (2×) and DCM (2×) and a Kaiser Resin test was conducted to determine if the coupling was complete. The Fmoc deprotection and coupling sequence was repeated until the desired peptide was assembled.

After the final Fmoc deprotection, the resin was transferred to a 15 mL falcon tube and put under vacuum to dry for several hours. The peptide was deprotected and cleaved from the solid support by exposing the resin to a solution of 95% TFA and 5% triisopropylsilane. The mixture mixed on a Labquake™ rotator for 24 h at room temperature. The solution was then filtered to remove the resin and concentrated under pressure for 30 min to produce an oil. To the oil was added ~0.5 mL cold (0° C.) diethyl ether. The material was pelleted via centrifugation, and the ether layer was removed. The pellet was washed two additional times with dry diethyl ether before drying under vacuum. The crude peptide was dissolved in TFA/water then purified by RP-HPLC (5-70% CH$_3$CN/H$_2$O with 0.1% TFA over 30 min) to afford a white solid after lyophilization.

$^1$H-NMR (CD$_3$OD, 600 MHz): δ 8.32-8.16 (m, 4H), 4.37-4.35 (m, 3H), 4.30-4.28 (m, 1H), 3.21 (s, 8H), 2.92 (t, J=7.5 Hz, 2H), 2.30 (t, J=7.4 Hz, 2H), 1.92-1.66 (m, 20H), 1.44-1.39 (m, 2H) ppm.

HRMS (ES+m/z): Calculated for C$_{30}$H$_{63}$N$_{18}$O$_5$$^+$: 755.5278 (M+H). Found: 755.5213 (M+H).

T$_R$: 6 minutes.

V-r4. Synthesized following the same procedure as V-r8. Purified by RP-HPLC on a Semi-Prep column with 5-70-100% CH$_3$CN/H$_2$O with 0.1% TFA over 40 min. The appropriate fractions were lyophilized and the product was isolated as a TFA salt (41% yield). The compound was stored as frozen aliquots in MQ water at −20° C. Defrosted aliquots would be used within 24 h for experiments. Concentration of aliquots were determined using Nanodrop UV-Vis spectrometer based on Beer's Law (λ=280 nm for vancomycin, c=4200, path length=1 mm).

$^1$H-NMR (CD$_3$OD, 500 MHz): δ 7.67 (t, J=31.0 Hz, 3H), 7.29 (s, 2H), 7.16-6.95 (m, 1H), 6.87 (s, 1H), 6.61-6.26 (m, 1H), 5.81 (s, 1H), 5.38 (d, J=55.8 Hz, 4H), 4.83-4.61 (m, 1H), 4.59-4.16 (m, 2H), 4.10 (s, 1H), 3.98-3.73 (m, 2H), 3.71-3.57 (m, 1H), 3.57-3.49 (m, 1H), 3.47 (q, J=1.7 Hz, 1H), 3.26-3.10 (m, 4H), 3.02 (s, 1H), 3.00-2.90 (m, 1H), 2.90-2.87 (m, 1H), 2.86-2.81 (m, 1H), 2.78 (d, J=7.2 Hz, 2H), 2.41-2.22 (m, 1H), 2.19-1.99 (m, 1H), 1.68 (s, 5H), 1.52 (s, 1H), 1.46-1.38 (m, 1H), 1.38-1.28 (m, 1H), 1.22 (s, 3H), 1.09-0.94 (m, 6H) ppm.

$^{19}$F-NMR: (CD$_3$OD, 376 MHz): δ-76.9 ppm.

HRMS (ES+m/z): Calculated for C$_{96}$H$_{137}$C$_{12}$N$_{27}$O$_{28}$$^{2+}$: 1093.4837 (M+2H)/2, C$_{96}$H$_{138}$C$_{12}$N$_{27}$O$_2$$^{3+}$: 729.3210(M+3H)/3. Found: 1094.0117 (M+2H)/2, 729.2594 (M+3H)/3.

T$_R$: 15 minutes.

V-r8 HCl Salt

To the V-r8 TFA salt (11.9 mg) was added biological-grade water (12 mL). To this solution was added 100 mM HCl (aq) for a final concentration of ~10 mM. The solution sat at room temperature for one minute, then was lyophilized overnight. This procedure was repeated twice more. The product was confirmed by the absence of a peak by $^{19}$F-NMR. The compound was stored as frozen aliquots in MQ water at −20° C. Defrosted aliquots would be used within 24 h for experiments. Concentration of aliquots were determined using Nanodrop UV-Vis spectrometer based on Beer's Law (λ=280 nm for vancomycin, c=4200, path length=1 mm).

FITC-V$^5$_Vancomycin-HCl (16.1 mg, 0.011 mmol, 1.0 equiv) was dissolved in 2.5 mL bicarbonate buffer (Na$_2$CO$_3$/NaHCO$_3$, pH=10) in an oven dried vial charged with a stir bar. FITC (25 mg, 0.064 mmol, 6.0 equiv) was dissolved in 25 μL DMSO and added to the vancomycin vial. Orange precipitate formed immediately. The reaction was stirred at 4° C. overnight. The reaction mixture was filtered and purified by RP-HPLC, 10-30-90% CH$_3$CN/H$_2$O with 0.1% TFA over 30 min. The appropriate fractions were isolated and lyophilized to afford an orange powder (55% yield).

HRMS (ES+m/z): Calculated for C$_{87}$H$_{86}$C$_{12}$N$_{10}$O$_{29}$S$^+$: 1836.47 (M+H). Found: 1839.4638 (M+H) and 1696.3789 (M-glucose+H, matched with literature)$^5$ T$_R$: 11.7 minutes.

FITC-V-r8 V-r8 conjugate (3) (12.0 mg, 0.0037 mmol, 1.0 equiv) was dissolved in 1.8 mL bicarbonate buffer (Na$_2$CO$_3$/NaHCO$_3$, pH=10) in an oven dried vial charged with a stir bar. FITC (8.9 mg, 0.023 mmol, 6.0 equiv) was dissolved in a separate vial in 10 μL DMSO and added. Reaction was stirred at 4° C. for 36 h and monitored by LC/MS. The reaction mixture was filtered and purified by RP-HPLC 10-90% CH$_3$CN/H$_2$O with 0.1% TFA over 30 min. The appropriate fractions were isolated and lyophilized to afford an orange powder (23% yield).

MALDI-MS (m/z): Calculated 1020.28 (M-glucose+3H)/3. Found: 1020.98.

T$_R$: 10 minutes.

Determination of MICs. MICS were determined using broth microdilution in accordance with CLSI methods.$^6$ One day prior to each MIC experiment, bacterial strains were streaked for single colonies from frozen glycerol stocks stored at −80° C. on Tryptic soy agar. 3-5 colonies from each plate were harvested with a disposable inoculating loop and resuspended in 500 μL PBS. This suspension was diluted in sterile-filtered PBS to an OD of 0.1(~1×10$^8$ CFU/ml), and the OD 0.1 suspension was diluted 1:100 in Mueller-Hinton Broth (MHB, Difco 257530) just prior to inoculating the 96-well polypropylene treatment plate. The treatment plate was prepared as follows: 20-fold stocks of the highest concentration of compound tested were prepared in sterile-filtered PBS and were subsequently diluted in MHB to prepare working stocks at 2-times the final concentration. 100 μL of each working stock was placed in the highest concentration treatment well, and the working stocks were 2-fold serially diluted in MHB to lend final treatment volumes of 50 µL/well. 50 µL of adjusted inoculum was added to each well to lend a total volume of 100 µL/well and a final inoculum density of ~5×10$^5$ colony forming units (CFU/ml). 10 µL of inoculum in growth control wells was serially diluted in PBS and plated on Tryptic soy agar to verify accurate starting density of cells. Growth controls were included in each plate, where no treatment was applied, along with media only controls. Edge wells were filled with PBS. The completed assay plate was sealed with parafilm, placed in a lidded plastic tray lined with moistened paper towels, and incubated at 37° C. for 18-20 h. The values reported are median values from a minimum of two experiments performed on different days.

Determination of MBECs. Minimum Biofilm Eradication Concentrations (MBECs) were determined in accordance with literature methods. Prior to each assay, 4 mL Tryptic Soy broth (TSB) was inoculated with one colony of *S. aureus* 29213, MW2 or USA300 and incubated at 37° C., 200 rpm shaking until stationary phase was reached (OD>2). The cultures were adjusted to in TSB to achieve a final inoculum density of 1×10$^7$ CFU/ml, and 150 µL of inoculum was added to each well of a 96-well base plate (Nunc™ 269787), and a plate lid containing 96 pegs (Nunc™ 445497) was added to the base. The entire apparatus was sealed with parafilm and placed in a sealed plastic bag lined with moistened paper towels for 48 h growth with shaking (150 rpm) at 35° C.

To prepare biofilm treatment plates, 20-fold stocks of the highest concentration tested were made in sterile-filtered PBS. The 20-fold stocks were diluted in TSB to yield 2-fold working stocks; 200 µL of working stock was added to the highest concentration treatment well and 2-fold serially diluted across the plate to lend final treatment volumes of 100 µL/well. TSB was added to treatment wells to yield final volume of 200 µL/well. PBS was added to the edge wells of the 96-well plate.

Prior to treatment, 48 h biofilms were rinsed in a 96-well plate containing 200 µL PBS/well for one minute and then the peg lid was transferred to the treatment plate. The plate was parafilmed and incubated at 35° C. for 24 h with 150 rpm shaking. Upon 24 h treatment, the peg lid was removed, rinsed in 200 µL PBS buffer twice for 1 min each, then transferred to a recovery plate containing 200 µL TSB+1% Tween-20 per well. The apparatus was placed in a steel tray and sonicated in a water bath sonicator (Branson 1510) for 10 min to dislodge biofilms. The peg lid was subsequently removed and the media-containing plate was incubated for 20 h at 35° C. with 150 rpm shaking to recover biofilms. The MBEC was read as the lowest treatment concentration where no growth occurred, as determined by measuring by OD600 on a plate reader. The values reported are median values from a minimum of two experiments performed on different days.

Evaluation of antibacterial activity against persister cells. USA300 persister cells were generated by diluting an overnight culture of USA300 bacteria 1:1000 in 4 mL MHB and growing to OD 0.5 at 37° C. with 200 rpm shaking. The OD 0.5 culture was treated with 10×MIC of ciprofloxacin (40 µM treatment) for 6 h at 37° C., 200 rpm shaking, and 20 µL culture aliquots were taken every 2 h, serially diluted in PBS, and plated on Tryptic soy agar to enumerate CFU/ml. Upon 6 h treatment with ciprofloxacin, 500 µL culture aliquots were added to Eppendorf tubes and compounds were added from concentrated stocks (mM range) to yield desired final concentrations (10-20 µM). The aliquots were incubated at 37° C. with 200 rpm shaking. CFU/ml were plated at indicated time points to monitor treatment efficacy. The experiment was performed at least twice on separate days.

Monitoring of antimicrobials in murine skin wound excisional model. Wound infections were performed as previously described, with minor modifications. Briefly, male wild-type C57BL/6 mice (7-8 weeks old, 22 to 25 g, InVivos, Singapore) were anesthetized in an induction chamber supplied with 3% isoflurane. Anesthetization was maintained with a nose cone throughout the procedure. Dorsal hair of the mice was removed by trimming and applying hair removal cream (Nair™ cream, Church and Dwight Co, Charles Ewing Boulevard, USA). The trimmed hair was then gently removed using a scalpel blade. Skin was disinfected with 70% ethanol and excised with a 6 mm biopsy punch (Integra Miltex, New York, USA). A 10 µ drop of PBS containing 7×10$^4$ CFU of USA300 LAC was inoculated directly onto the open wound surface. The inoculum was allowed to dry before applying an 8 mm Finn Chamber® (SmartPractice, Phoenix, AZ) over it and sealed with an additional transparent dressing (Tegaderm™ 3M, St Paul Minnesota, USA). Mice were monitored for signs of pain and distress, and analgesics were administered as necessary. After 24 h infection, the wound dressing was removed without physically affecting the skin layer. 10 µl PBS containing vancomycin, V-r8 HCl, fusidic acid (Sigma-Aldrich)), or water (negative control) was added to infected wounds at the indicated concentrations, followed by reapplication of Tegaderm. After 5 hours, an area of 1 cm×1 cm of skin surrounding the wound site was excised and collected in sterile PBS. Skin samples were homogenized, serially diluted, and plated on tryptic soy broth (TSB) plates containing 1.5% agar and MRSASelect™ II agar plates (Bio-Rad, USA) for selective viable USA300 enumeration to determine the efficacy of bacterial clearance post-treatment. Wound contaminated with non-USA300 bacteria was monitored by growth on TSB agar plates containing no antibiotics for selection and were excluded from analysis.

In vivo histological cytotoxicity assessment. To assess the toxicity of V-r8 HCl, skin wounds were created in male wild-type C57BL/6 mice (7-8 weeks old, 22 to 25 g, InVivos, Singapore) while anesthetized in an induction chamber supplied with 3% isoflurane (same as described above) Uninfected wounds were administered with 10 µl of water or 0.05% of V-r8 immediately after wounding and excised after 3 days as described above. Samples were fixed in 4% paraformaldehyde in PBS and incubated in 20% sucrose for 24 hours. Tissues were then embedded into Optical Cutting Temperature (OCT) compound (Sakura, California) and snap frozen in liquid nitrogen. 12 µm sections were obtained on a Leica CM1860 UV cryotome (Leica Biosystems, Ernst-Leitz Strasse, Germany), stained with hemotoxylin and eosin (H&E), and visualized using an Axio Scan.Z1 slide scanner (Carl Zeiss, Göttingen, Germany) under 20×/0.8 Apochrome objective as previously described.

Statistical analysis. Statistical analysis of animal data between treated and non-treated groups was performed using the non-parametric Kruskal-Wallis test with Dunn's post ad hoc test for intergroup comparisons.

Time-Kill Kinetics Experiments in MHB and PBS. A stationary-phase culture of USA400 MW2 was prepared by inoculating 1 colony into 4 mL media and growing at 37° C. for 14-16 h. The culture was pelleted 3 times by centrifugation at 10,000 g for 1 min to remove spent medium and diluted in PBS to OD 0.1 just prior to treatment. 50 µL of the bacterial suspension was mixed with 50 µL of treatment compounds at 2-times the desired concentration for a final treatment concentration of 20 µM. The plate was incubated at 37° C. with 200 rpm shaking, and CFUs were plated on Tryptic soy agar via serial dilution at determined time points. Lysostaphin (1.25 µg/mL) served as a positive control. The experiment was performed twice on separate days.

For time-kill studies performed in MHB, a stationary phase culture of USA400 MW2 was diluted to $1\times10^6$ CFU/ml and 50 µL of this suspension was mixed with 50 µL of MHB containing 2 times of the desired final concentrations of compounds. The plate was incubated at 37 degrees with 200 rpm shaking, and CFUs were plated on Tryptic soy agar at determined time points. The experiment was performed twice on separate days.

Evaluation of Bacterial Membrane Integrity with SYTOX Green. The SYTOX Green assay was adapted from the literature. Briefly, to a black wall clear-bottom 96-well plate (Costar 3603) was added 50 µL of PBS per well containing antibiotics at 2-times the indicated concentration. 1 mL of a stationary phase MW2 culture was pelleted at 10,000 g for 1 min and washed 3 times with the same volume of sterile-filtered PBS. The washed cells were diluted to $OD_{600}=0.1$ ($\sim4\times10^7$ CFU/mL) with PBS. SYTOX Green (Molecular Probes) was added to the diluted stationary phase suspension for a final concentration of 5 µM and incubated for 0.5 h at room temperature in the dark. 50 µL of the bacteria/SYTOX Green mixture was added to each well of 96-well plates containing antibiotics and fluorescence was measured at 37° C. with shaking for up to 4 h using a spectrophotometer (SpectraMax M3, Molecular Devices) with excitation and emission wavelengths of 485 and 525 nm, respectively. Lysostaphin (1.25 µg/mL) was used as a positive control. The experiment was performed twice on separate days.

Flow cytometry experiments. OD 0.5 pellets were prepared from stationary-phase USA400 MW2 cultures via centrifugation of culture at 8000 rpm for 5 min followed by aspiration of supernatant. The pellets were resuspended in PBS buffer and desired concentrations of fluorescent compound were added, for a final treatment volume of 500 µL. Samples were incubated for 5 min at 37° C. in the dark. Upon completion of treatment, the samples were immediately centrifuged at 8000 rpm for 5 min to remove unbound compound and the supernatant in each sample was aspirated. The pelleted bacteria were resuspended in 400 µL PBS and transferred into round bottom polystyrene sample tubes (Falcon, Cat. No. 352058). Flow cytometry experiments were then performed on a FACScan flow cytometer at 488 nm. For trypan blue quenching experiment, 10% v/v of 2 mM trypan blue was added to bacteria and incubated for 5-10 min before analysis.

For protoplast FACS experiments, treated cell pellets were resuspended in PBS buffer supplemented with 1 M sucrose and 75 µg/ml lysostaphin for 1 h at 37° C., 200 rpm. The efficacy of protoplast treatment was assessed by diluting culture 1:4 in PBS and measuring the OD600 to confirm lysis of cells. The resultant protoplast suspension analyzed by FACS.

Confocal microscopy. Stationary-phase cultures of USA400 MW2 in TSB were diluted 1:20, then spotted onto poly-L-lysine coated slides for 15 minutes. Non-adherent bacteria were aspirated and adherent bacteria were washed with PBS. Adherent bacteria were incubated with 5 µM treatment in PBS at room temperature for 5 minutes in the dark, then washed with PBS. For quenching experiments, samples were treated with 0.2% Trypan Blue after FITC-compound treatments for 5 minutes at room temperature, then washed with PBS. All samples were imaged on a Zeiss LSM 700 confocal microscope with an EC Plan-Neofluar 40×/0.75 oil-immersion objective. Images in each experiment were taken with identical laser intensities and processed in Fiji (Image J) with the same settings. Experiments were performed twice on different days.

Example 2

Activity Against Gram-Negative Cells

V-r8 and vancomycin (V) demonstrated no efficacy at therapeutically relevant concentrations in *P. aeruginosa, H. pylori*, and *A. baumannii* (Table 5, latter two strains not shown but the MICs were >32 µM). Interestingly, V-r8 demonstrated antimicrobial activity against *V. cholerae*, a pathogenic Gram-negative strain responsible for cholera disease, and modest activity in a pathogenic *E. coli* strain responsible for urinary tract infections. However, in the *E. coli* strain the MIC of V-r8 correlated strongly with the MIC of r8 alone and a 1:1 noncovalent mixture of V and r8, suggesting that V-r8's activity is due to the r8 portion of V-r8. V-r8's activity in *V. cholerae* is far superior to that of r8 or vancomycin (or even noncovalent V+r8) alone, suggesting that it is the covalent conjugation of the two molecules that provides the increase in activity. Therefore V-r8 appears to have selective antimicrobial activity against *V. cholerae* amongst a panel of Gram-negative bacterial strains.

TABLE 5

Median MIC values in uM required to eradicate Gram-negative planktonic strains in vitro. Data was obtained from a minimum of two independent trials unless otherwise noted.

| Strain | V | V − r8 | r8 | V + r8 | V − r4 |
|---|---|---|---|---|---|
| *V. cholerae* El Tor A1552R | 100 | 10 | >80 | 80 | 32 |
| *E. coli* UTI89 | >128 | ≥32 | 36 | 40[a] | >64 |
| *P. aeruginosa* PA14[a] | >256 | >32 | ND | ND | >32 |

ND = not determined;
[a]values are from one trial only.

Time-kill assays were used to explore the compounds' rate of killing. At equivalent concentrations, V-r8 outperformed V, r8 and untreated cells by almost 5 orders of magnitude after 4 h. Additionally, V-r8 demonstrated 2-3 orders of magnitude higher killing than kanamycin, an aminoglycoside antibiotic, at equivalent concentrations over the first 2 h. These results confirm that V-r8 can act on actively growing (in media) or stationary cells (in PBS) and that V-r8 is acting faster than kanamycin.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A method of reducing bacterial load, the method comprising
contacting a bacterial cell population that comprises one or more of:
persister cells, and MRSA biofilms, with an effective dose non-toxic to human cells of a conjugate comprising an antibiotic selected from vancomycin, oritavancin, and dalbavancin, conjugated at the carboxy terminus directly or through a linker to a guanidinium-rich molecular transporter (GR-MoTr), wherein the GR-MoTr consists of from about 4 to about 9 arginines, which may be L-arginine, D-arginine, or a combination thereof; wherein the bacterial cell populations comprises at least 10% of one or more of persister cells, and MRSA biofilm cells.

2. The method of claim 1, wherein the antibiotic has the structure:

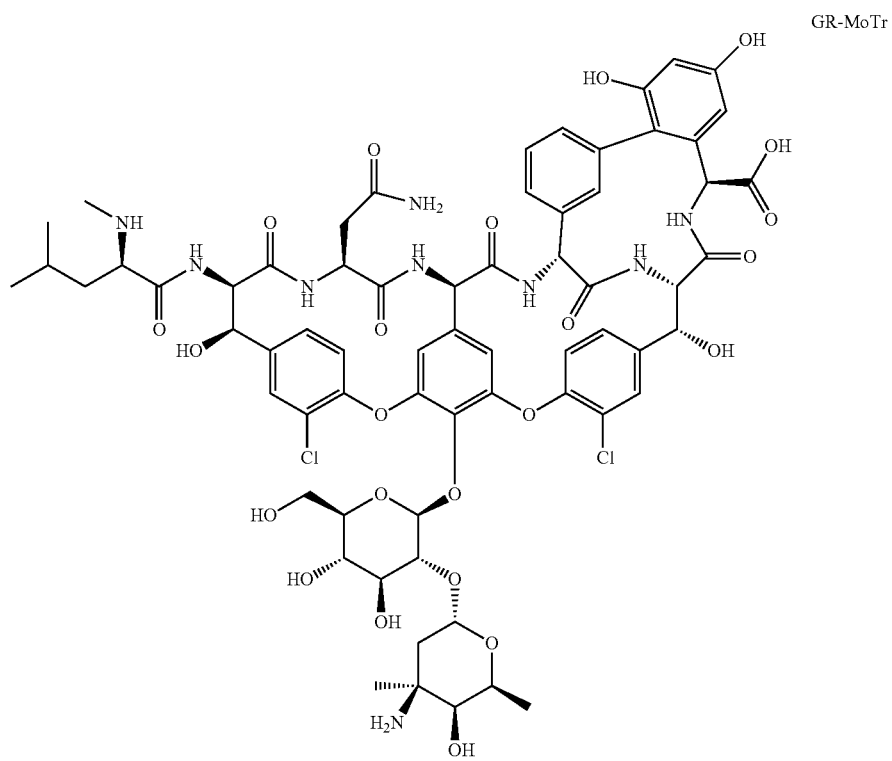 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cccc3c4)[C@H](O)c3ccc(c(Cl)c3)Oc3cc2cc(c3O[C@@H]2O[C@H](CO)[C@@H](O)[C@H](O)[C@H]2O[C@H]2C[C@](C)(N)[C@H](O)[C@H](C)O2)Oc2ccc(cc2Cl)[C@H]1O]

wherein the GR-MoTr is D-octa-arginine, optionally joined through a linker, and optionally comprising a counter-ion.

3. The method of claim 1, wherein the bacterial cell population is tested for the presence of one or more of:
persister cells, and MRSA biofilm prior to said contacting step.

4. The method of claim 1, wherein the bacterial cell population comprises at least 10 percent persister cells, and the antibiotic conjugated to GR-MoTr provides for an effectiveness of at least 1000-fold relative to unconjugated antibiotic.

5. The method of claim 1, wherein the bacterial cell population comprises at least 10 percent of MRSA biofilm cells, and the antibiotic conjugated to GR-MoTr provides for an effectiveness of at least 10-fold relative to unconjugated antibiotic.

6. A method of reducing bacterial load, the method comprising
contacting a bacterial cell population that comprises Vibrio cholerae with an effective dose non-toxic to human cells of a conjugate comprising vancomycin, oritavancin, or dalbavancin, conjugated directly or through a linker to a guanidinium-rich molecular transporter (GR-MoTr), wherein the GR-MoTr consists of from about 4 to about 9 arginines, which may be L-arginine, D-arginine, or a combination thereof.

7. The method of claim 6, wherein the antibiotic has the structure:
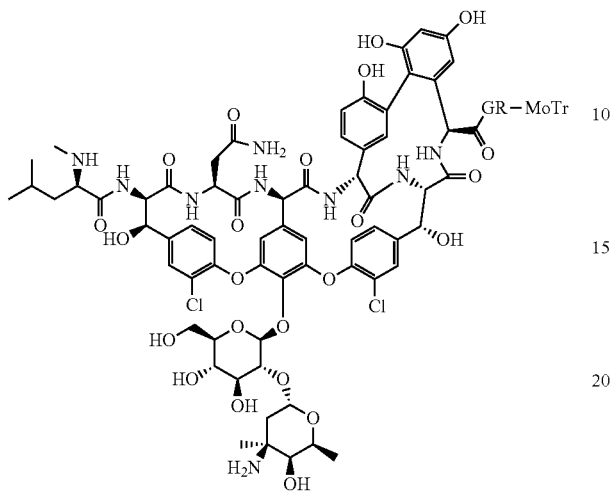
wherein the GR-MoTr is D-octa-arginine, optionally joined through a linker, and optionally comprising a counter-ion.
* * * * *

UNITED STATES PATENT AND TRADEMARK OFFICE
CERTIFICATE OF CORRECTION

| | | |
|---|---|---|
| PATENT NO. | : 12,194,105 B2 | Page 1 of 1 |
| APPLICATION NO. | : 16/968834 | |
| DATED | : January 14, 2025 | |
| INVENTOR(S) | : Melanie Huttner et al. | |

It is certified that error appears in the above-identified patent and that said Letters Patent is hereby corrected as shown below:

In the Specification

Column 1, Line 16 please add the "STATEMENT OF GOVERNMENT SUPPORT" with the following text:
--Statement of Government Support
This invention was made with Government support under contracts CA031845 and GM117278 awarded by the National Institutes of Health. The Government has certain rights in the invention.--

Signed and Sealed this
Twenty-fifth Day of February, 2025

Coke Morgan Stewart
*Acting Director of the United States Patent and Trademark Office*